US012758336B2

(12) United States Patent
Di Guardo et al.

(10) Patent No.: US 12,758,336 B2
(45) Date of Patent: Oct. 13, 2026

(54) METHOD FOR CONTROLLING A ROBOTIC SYSTEM FOR MEDICAL OR SURGICAL TELEOPERATION, HAVING A MECHANICALLY UNCONSTRAINED MASTER DEVICE BEING MOVABLE BY AN OPERATOR, WITH CONTROL OF LOCAL REFERENCE COORDINATE FRAMES AND ROBOTIC SYSTEM USING THE METHOD

(71) Applicant: MEDICAL MICROINSTRUMENTS, INC., Wilmington, DE (US)

(72) Inventors: Antonio Di Guardo, Pisa (IT); Matteo Tanzini, Pisa (IT); Massimiliano Simi, Pisa (IT); Emanuele Ruffaldi, Pisa (IT); Michael John Proctor, Pisa (IT); Giuseppe Maria Prisco, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 395 days.

(21) Appl. No.: 18/546,225

(22) PCT Filed: Feb. 11, 2022

(86) PCT No.: PCT/IB2022/051244
§ 371 (c)(1),
(2) Date: Aug. 11, 2023

(87) PCT Pub. No.: WO2022/175795
PCT Pub. Date: Aug. 25, 2022

(65) Prior Publication Data

US 2024/0115337 A1 Apr. 11, 2024

(30) Foreign Application Priority Data

Feb. 16, 2021 (IT) ........................ 102021000003479

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/37* (2016.02); *A61B 34/74* (2016.02); *A61B 90/06* (2016.02); *A61B 2090/067* (2016.02)

(58) Field of Classification Search
CPC ......... A61B 34/35; A61B 34/37; A61B 34/74; A61B 90/06; A61B 2090/067;
(Continued)

(56) References Cited

U.S. PATENT DOCUMENTS 5,943,914 A 8/1999 Morimoto
6,063,095 A 5/2000 Wang
(Continued)

FOREIGN PATENT DOCUMENTS

CN 108451643 A 8/2018
DE 102010009065 A1 8/2011
(Continued)

OTHER PUBLICATIONS

International Search Report and Written Opinion received for PCT Serial No. PCT/IB2022/051226 on Apr. 8, 2022, 15 pgs.
(Continued)

*Primary Examiner* — Harry Y Oh
(74) *Attorney, Agent, or Firm* — Merchant & Gould P.C.

(57) ABSTRACT

A method initiates and/or prepares and/or conducts teleoperation by a robotic system for medical or surgical teleoperation. The robotic system includes a master device, which is hand-held, mechanically unconstrained and moveable by an operator, and a slave device including a surgical instrument controlled by the master device. The master device is functionally symmetrical with respect to a predeterminable
(Continued)

single, longitudinal axis of the master device. A local reference frame of the master device and the related longitudinal axis is detected, with respect to a main reference frame of the master device workspace; then, functionally equivalent local reference frames are detected. A corresponding target reference frame is mapped in a workspace of the slave device. An operating reference frame is detected according to criteria for optimization of the trajectory of the slave device. A robotic system for medical or surgical teleoperation is control led by the control method.

20 Claims, 7 Drawing Sheets

(51) Int. Cl.

| | |
|---|---|
| ***A61B 34/37*** | (2016.01) |
| ***A61B 90/00*** | (2016.01) |
| ***B25J 9/16*** | (2006.01) |
| ***B25J 13/02*** | (2006.01) |

(58) Field of Classification Search

CPC .... A61B 2090/3937; A61B 2090/3954; G05B 2219/39065; G05B 2219/40401; B25J 9/1689; B25J 13/02

See application file for complete search history.

(56) References Cited

U.S. PATENT DOCUMENTS

| | | | |
|---|---|---|---|
| 6,364,888 | B1 | 4/2002 | Niemeyer |
| 6,424,885 | B1 | 7/2002 | Niemeyer |
| 6,459,926 | B1 | 10/2002 | Nowlin |
| 6,594,552 | B1 | 7/2003 | Nowlin |
| 6,671,581 | B2 | 12/2003 | Niemeyer |
| 6,766,204 | B2 | 7/2004 | Niemeyer |
| 6,879,880 | B2 | 4/2005 | Nowlin |
| 7,087,049 | B2 | 8/2006 | Nowlin |
| 7,155,315 | B2 | 12/2006 | Niemeyer |
| 7,331,967 | B2 | 2/2008 | Lee |
| 7,373,219 | B2 | 5/2008 | Nowlin |
| 7,778,733 | B2 | 8/2010 | Nowlin |
| 7,806,891 | B2 | 10/2010 | Nowlin |
| 7,886,743 | B2 | 2/2011 | Cooper |
| 7,947,050 | B2 | 5/2011 | Lee |
| 7,967,137 | B2 | 6/2011 | Fulbrook |
| 8,004,229 | B2 | 8/2011 | Nowlin |
| 8,005,571 | B2 | 8/2011 | Sutherland |
| 8,123,740 | B2 | 2/2012 | Madhani |
| 8,220,468 | B2 | 7/2012 | Cooper |
| 8,281,670 | B2 | 10/2012 | Larkin |
| 8,368,649 | B2 | 2/2013 | Hall |
| 8,375,808 | B2 | 2/2013 | Blumenkranz |
| 8,521,331 | B2 | 8/2013 | Itkowitz |
| 8,540,748 | B2 | 9/2013 | Murphy |
| 8,543,240 | B2 | 9/2013 | Itkowitz |
| 8,620,473 | B2 | 12/2013 | Diolaiti |
| 8,638,057 | B2 | 1/2014 | Goldberg |
| 8,677,820 | B2 | 3/2014 | Nakagawa |
| 8,812,160 | B2 | 8/2014 | Hagn |
| 8,831,782 | B2 | 9/2014 | Itkowitz |
| 8,935,003 | B2 | 1/2015 | Itkowitz |
| 8,939,963 | B2 | 1/2015 | Rogers |
| 8,996,173 | B2 | 3/2015 | Itkowitz |
| 9,060,796 | B2 | 6/2015 | Seo |
| 9,101,379 | B2 | 8/2015 | Au |
| 9,333,042 | B2 | 5/2016 | Diolaiti |
| 9,387,043 | B2 | 7/2016 | Yang |
| 9,408,668 | B2 | 8/2016 | Durant |
| 9,452,020 | B2 | 9/2016 | Griffiths |
| 9,492,927 | B2 | 11/2016 | Diolaiti |
| 9,554,866 | B2 | 1/2017 | Cunningham |
| 9,629,680 | B2 | 4/2017 | Winer |
| 9,632,573 | B2 | 4/2017 | Ogawa |
| 9,707,684 | B2 | 7/2017 | Ruiz Morales |
| 9,743,989 | B2 | 8/2017 | Itkowitz |
| 9,770,300 | B2 | 9/2017 | Kwon |
| 9,855,662 | B2 | 1/2018 | Ruiz Morales |
| 9,901,402 | B2 | 2/2018 | Itkowitz |
| 9,949,799 | B2 | 4/2018 | Hingwe |
| 9,968,405 | B2 | 5/2018 | Cooper |
| 10,013,082 | B2 | 7/2018 | Schecter |
| 10,034,718 | B2 | 7/2018 | Griffiths |
| 10,052,164 | B2 | 8/2018 | Overmyer |
| 10,085,810 | B2 | 10/2018 | Vakharia |
| 10,123,844 | B2 | 11/2018 | Nowlin |
| 10,188,472 | B2 | 1/2019 | Diolaiti |
| 10,219,870 | B2 | 3/2019 | Mondry |
| 10,219,898 | B2 | 3/2019 | Forsell |
| 10,271,915 | B2 | 4/2019 | Diolaiti |
| 10,292,661 | B1 | 5/2019 | LaBorde |
| 10,299,873 | B2 | 5/2019 | Hares |
| 10,299,883 | B2 | 5/2019 | Kilroy |
| 10,307,199 | B2 | 6/2019 | Farritor |
| 10,321,964 | B2 | 6/2019 | Grover |
| 10,357,320 | B2 | 7/2019 | Beira |
| 10,357,324 | B2 | 7/2019 | Flatt |
| 10,376,323 | B2 | 8/2019 | Farritor |
| 10,376,337 | B2 | 8/2019 | Kilroy |
| 10,383,699 | B2 | 8/2019 | Kilroy |
| 10,393,109 | B2 | 8/2019 | Wu |
| 10,413,374 | B2 | 9/2019 | Chassot |
| 10,420,618 | B2 | 9/2019 | Grover |
| 10,470,830 | B2 | 11/2019 | Hill |
| 10,485,621 | B2 | 11/2019 | Morrissette |
| 10,512,514 | B2 | 12/2019 | Nowlin |
| 10,512,515 | B2 | 12/2019 | Bailey |
| 10,524,871 | B2 | 1/2020 | Liao |
| 10,531,929 | B2 | 1/2020 | Widenhouse |
| 10,543,050 | B2 | 1/2020 | Itkowitz |
| 10,561,468 | B2 | 2/2020 | Cunningham |
| 10,568,703 | B2 | 2/2020 | Nobles |
| 10,568,704 | B2 | 2/2020 | Savall |
| 10,603,123 | B2 | 3/2020 | Vakharia |
| 10,617,484 | B2 | 4/2020 | Kilroy |
| 10,624,708 | B2 | 4/2020 | Hunter |
| 10,639,114 | B2 | 5/2020 | Schuh |
| 10,653,489 | B2 | 5/2020 | Kopp |
| 10,661,453 | B2 | 5/2020 | Koenig |
| 10,736,701 | B2 | 8/2020 | Savall |
| 10,736,706 | B2 | 8/2020 | Scheib |
| 10,751,136 | B2 | 8/2020 | Farritor |
| 10,758,298 | B2 | 9/2020 | Felder |
| 10,779,898 | B2 | 9/2020 | Hill |
| 10,786,327 | B2 | 9/2020 | Anderson |
| 10,789,329 | B2 | 9/2020 | Lanting |
| 10,813,713 | B2 | 10/2020 | Koch |
| 10,820,953 | B2 | 11/2020 | Kralicky |
| 10,842,577 | B2 | 11/2020 | Kilroy |
| 10,842,581 | B2 | 11/2020 | Bailey |
| 10,881,477 | B1 | 1/2021 | Genova |
| 10,888,390 | B2 | 1/2021 | Higuchi |
| 10,898,281 | B2 | 1/2021 | Cooper |
| 10,912,618 | B2 | 2/2021 | Vakharia |
| 10,959,798 | B2 | 3/2021 | Diolaiti |
| 10,987,192 | B2 | 4/2021 | Garcia Kilroy |
| 11,037,464 | B2 | 6/2021 | Ho |
| 11,045,268 | B2 | 6/2021 | Grover |
| 11,083,532 | B2 | 8/2021 | Liao |
| 11,083,534 | B2 | 8/2021 | Hares |
| 11,096,746 | B2 | 8/2021 | Savall |
| 11,109,925 | B2 | 9/2021 | Cooper |
| 11,135,031 | B2 | 10/2021 | Savall |
| 11,172,997 | B2 | 11/2021 | Kostrzewski |
| 11,179,209 | B2 | 11/2021 | Kralicky |
| 11,179,211 | B2 | 11/2021 | Zemlok |
| 11,179,213 | B2 | 11/2021 | Huang |
| 11,213,364 | B2 | 1/2022 | Popovic |
| 11,246,670 | B2 | 2/2022 | Swayze |
| 11,266,469 | B2 | 3/2022 | Fuerst |
| 11,284,957 | B2 | 3/2022 | Denlinger |
| 11,284,959 | B2 | 3/2022 | Bailey |

(56) References Cited

U.S. PATENT DOCUMENTS 11,344,374 B2 5/2022 Tekiela
11,357,597 B2 6/2022 Jhaveri
11,399,908 B2 8/2022 Diolaiti
11,406,465 B2 8/2022 Zemlok
11,439,478 B2 9/2022 Anderson
11,446,097 B2 9/2022 Savall
11,457,987 B2 10/2022 He
11,478,318 B2 10/2022 Cone
11,478,928 B2 10/2022 Hariri
11,484,379 B2 11/2022 Sutherland
11,504,197 B1 11/2022 Noonan
11,504,203 B2 11/2022 Flatt
11,534,246 B2 12/2022 Fuerst
11,534,252 B2 12/2022 DiMaio
11,576,733 B2 2/2023 Anglese
11,607,279 B2 3/2023 Chaplin
11,666,401 B2 6/2023 Denlinger
11,684,434 B2 6/2023 Shelton
11,707,336 B2 7/2023 Itkowitz
11,712,314 B2 8/2023 Thompson
12,048,505 B2 7/2024 Thompson
2002/0055795 A1 5/2002 Niemeyer
2002/0128552 A1 9/2002 Nowlin
2003/0004610 A1 1/2003 Niemeyer
2003/0195664 A1 10/2003 Nowlin
2004/0039485 A1 2/2004 Niemeyer
2005/0194507 A1 9/2005 White
2006/0030840 A1 2/2006 Nowlin
2006/0106493 A1 5/2006 Niemeyer
2006/0241414 A1 10/2006 Nowlin
2007/0013336 A1* 1/2007 Nowlin .................. A61B 34/30
318/568.21
2008/0114494 A1 5/2008 Nixon
2008/0154246 A1 6/2008 Nowlin
2009/0301927 A1 12/2009 Fulbrook
2010/0053085 A1 3/2010 Hall
2010/0094312 A1 4/2010 Ruiz Morales
2010/0274087 A1 10/2010 Diolaiti
2011/0118748 A1 5/2011 Itkowitz
2012/0011932 A1 1/2012 Nakagawa
2012/0059391 A1 3/2012 Diolaiti
2012/0071891 A1 3/2012 Itkowitz
2012/0071892 A1 3/2012 Itkowitz
2012/0316681 A1 12/2012 Hagn
2013/0012930 A1 1/2013 Ruiz Morales
2013/0035697 A1 2/2013 Ogawa
2013/0316681 A1 11/2013 Huang
2013/0321262 A1 12/2013 Schecter
2014/0018960 A1* 1/2014 Itkowitz ................. A61B 90/98
700/264
2014/0160015 A1 6/2014 Ogawa
2014/0171964 A1 6/2014 Yang
2014/0222021 A1 8/2014 Diolaiti
2015/0025549 A1 1/2015 Kilroy
2015/0038981 A1 2/2015 Kilroy
2015/0038982 A1 2/2015 Kilroy
2015/0066051 A1 3/2015 Kwon
2015/0080909 A1* 3/2015 Itkowitz ................. A61B 34/35
606/130
2015/0157410 A1 6/2015 Kilroy
2015/0182289 A1* 7/2015 Itkowitz ................. A61B 34/35
606/130
2016/0242860 A1 8/2016 Diolaiti
2016/0287279 A1 10/2016 Bovay
2017/0035521 A1 2/2017 Diolaiti
2017/0086931 A1* 3/2017 Auld ...................... A61B 34/37
2017/0095295 A1 4/2017 Overmyer
2017/0095298 A1 4/2017 Vakharia
2017/0156806 A1 6/2017 Prisco
2017/0224428 A1 8/2017 Kopp
2017/0252112 A1 9/2017 Crawford
2017/0265949 A1 9/2017 Crawford
2017/0312043 A1 11/2017 Ogawa
2017/0319284 A1 11/2017 Itkowitz
2018/0025666 A1 1/2018 Ho
2018/0036088 A1 2/2018 Kilroy
2018/0078034 A1 3/2018 Savall
2018/0078319 A1 3/2018 Nobles
2018/0078321 A1 3/2018 Liao
2018/0092706 A1 4/2018 Anderson
2018/0161108 A1 6/2018 Savall
2018/0168681 A1 6/2018 Kirk
2018/0168759 A1 6/2018 Kilroy
2018/0194013 A1 7/2018 Ruiz Morales
2018/0214223 A1 8/2018 Turner
2018/0235719 A1 8/2018 Jarc
2019/0012006 A1 1/2019 Schecter
2019/0029770 A1 1/2019 Bailey
2019/0069960 A1 3/2019 Vakharia
2019/0110847 A1 4/2019 Diolaiti
2019/0142530 A1 5/2019 Thompson
2019/0201152 A1 7/2019 Diolaiti
2019/0239972 A1 8/2019 Chassot
2019/0307524 A1 10/2019 Popovic
2019/0314097 A1 10/2019 Diolaiti
2019/0343594 A1 11/2019 Garcia Kilroy
2019/0380791 A1 12/2019 Fuerst
2019/0380802 A1 12/2019 Savall
2019/0380809 A1 12/2019 Fuerst
2019/0380971 A1 12/2019 Achkar
2020/0008901 A1 1/2020 Garcia Kilroy
2020/0015918 A1 1/2020 Payyavula
2020/0022775 A1 1/2020 Garcia Kilroy
2020/0046439 A1 2/2020 Tekiela
2020/0046450 A1 2/2020 Tsao
2020/0069388 A1 3/2020 Bailey
2020/0085522 A1 3/2020 Liao
2020/0113641 A1 4/2020 Itkowitz
2020/0138534 A1 5/2020 Garcia Kilroy
2020/0179068 A1 6/2020 Peine
2020/0194117 A1 6/2020 Krieger
2020/0197112 A1 6/2020 Chin
2020/0197115 A1 6/2020 Vakharia
2020/0205922 A1 7/2020 Cone
2020/0214773 A1 7/2020 Nobles
2020/0214778 A1 7/2020 Turner
2020/0214779 A1 7/2020 Masuda
2020/0222124 A1 7/2020 Savall
2020/0222134 A1 7/2020 Schuh
2020/0275985 A1 9/2020 Thompson
2020/0289212 A1 9/2020 Savall
2020/0289221 A1 9/2020 Denlinger
2020/0289223 A1 9/2020 Denlinger
2020/0330170 A1 10/2020 Farritor
2020/0360096 A1 11/2020 Savall
2020/0360097 A1 11/2020 DiMaio
2020/0390510 A1 12/2020 Thompson
2020/0397517 A1 12/2020 Unsworth
2020/0397529 A1 12/2020 Anderson
2020/0405408 A1 12/2020 Shelton
2020/0405434 A1 12/2020 Schuh
2021/0030495 A1 2/2021 Savall
2021/0052338 A1 2/2021 Hill
2021/0052341 A1 2/2021 Bailey
2021/0059781 A1 3/2021 Peine
2021/0085301 A1 3/2021 Au
2021/0121260 A1 4/2021 Genova
2021/0153964 A1 5/2021 Diolaiti
2021/0153965 A1 5/2021 Lau
2021/0153966 A1 5/2021 Lau
2021/0196411 A1 7/2021 Vakharia
2021/0196413 A1 7/2021 Inoue
2021/0197401 A1 7/2021 Weintraub
2021/0236220 A1 8/2021 Diolaiti
2021/0290326 A1 9/2021 Diolaiti
2021/0290328 A1 9/2021 Miller
2021/0298855 A1 9/2021 Thompson
2021/0304639 A1 9/2021 Ho
2021/0322117 A1 10/2021 Liao
2021/0322119 A1 10/2021 Hares
2021/0353381 A1 11/2021 Usui
2021/0369365 A1 12/2021 Goswami
2022/0015839 A1 1/2022 Savall
2022/0015852 A1 1/2022 Savall

(56) References Cited

U.S. PATENT DOCUMENTS

| | | | |
|---|---|---|---|
| 2022/0031415 | A1 | 2/2022 | Vargas |
| 2022/0047345 | A1 | 2/2022 | Choi |
| 2022/0096189 | A1 | 3/2022 | Popovic |
| 2022/0184823 | A1 | 6/2022 | Bonny |
| 2022/0192763 | A1 | 6/2022 | Fuerst |
| 2022/0202437 | A1 | 6/2022 | Overmyer |
| 2022/0211452 | A1 | 7/2022 | Clark |
| 2022/0218418 | A1 | 7/2022 | Jolaeimoghaddam |
| 2022/0226056 | A1 | 7/2022 | Beckman |
| 2022/0265380 | A1 | 8/2022 | Bailey |
| 2022/0361736 | A1 | 11/2022 | Danna |
| 2022/0361970 | A1 | 11/2022 | Griffiths |
| 2022/0370163 | A1 | 11/2022 | Schuh |
| 2022/0378526 | A1 | 12/2022 | Balicki |
| 2022/0378527 | A1 | 12/2022 | Basafa |
| 2022/0378533 | A1 | 12/2022 | McDiarmid |
| 2022/0387131 | A1 | 12/2022 | Anderson |
| 2022/0395346 | A1 | 12/2022 | Ihara |
| 2022/0401162 | A1 | 12/2022 | Unsworth |
| 2023/0028689 | A1 | 1/2023 | Rabindran |
| 2023/0045591 | A1 | 2/2023 | de la Fuente Klein |
| 2023/0149105 | A1 | 5/2023 | Thornycroft |
| 2023/0301738 | A1 | 9/2023 | Thompson |
| 2023/0355261 | A1 | 11/2023 | Yu |

FOREIGN PATENT DOCUMENTS

| | | | |
|---|---|---|---|
| DE | 102014006264 | A1 | 11/2015 |
| EP | 2845556 | A1 | 3/2015 |
| EP | 3245975 | A1 | 11/2017 |
| EP | 3424651 | A1 | 1/2019 |
| EP | 3459429 | A1 | 3/2019 |
| EP | 3574860 | A1 | 12/2019 |
| EP | 3852668 | | 7/2021 |
| JP | 2013034835 | | 2/2013 |
| JP | 2013049121 | | 3/2013 |
| JP | 2013049121 | A | 3/2013 |
| JP | 2013510671 | | 3/2013 |
| JP | 2013510671 | A | 3/2013 |
| JP | 2013510672 | | 3/2013 |
| JP | 2013510672 | A | 3/2013 |
| JP | 2016512733 | | 5/2016 |
| JP | 2016512733 | A | 5/2016 |
| JP | 2016514492 | | 5/2016 |
| JP | 2016514492 | A | 5/2016 |
| JP | 2017099820 | | 6/2017 |
| JP | 2019536556 | | 12/2019 |
| JP | 2020529237 | | 10/2020 |
| JP | 2021162200 | | 10/2021 |
| WO | 2013018861 | | 2/2013 |
| WO | 2013018861 | A1 | 2/2013 |
| WO | 2013071071 | A1 | 5/2013 |
| WO | 2014151621 | A1 | 9/2014 |
| WO | 2016053657 | A1 | 4/2016 |
| WO | 2016171757 | A1 | 10/2016 |
| WO | 2016201207 | A1 | 12/2016 |
| WO | 2017094844 | A1 | 6/2017 |
| WO | 2019220408 | A1 | 5/2018 |
| WO | 2018104252 | A1 | 6/2018 |
| WO | 2018107062 | A1 | 6/2018 |
| WO | 2018189725 | A1 | 10/2018 |
| WO | 2019027922 | | 2/2019 |
| WO | 2019050878 | A2 | 3/2019 |
| WO | 2019099584 | A1 | 5/2019 |
| WO | 2019103954 | A1 | 5/2019 |
| WO | 20200092170 | A1 | 10/2019 |
| WO | 2019220407 | A1 | 11/2019 |
| WO | 2019220409 | A1 | 11/2019 |
| WO | 2019240825 | A1 | 12/2019 |
| WO | 2020139405 | A1 | 7/2020 |
| WO | 2020153411 | A1 | 7/2020 |
| WO | 2021141920 | A1 | 7/2021 |
| WO | 2021188127 | A1 | 9/2021 |
| WO | 2022155067 | A1 | 7/2022 |

OTHER PUBLICATIONS

International Search Report and Written Opinion received for PCT Serial No. PCT/IB2022/051286 on Jun. 7, 2022, 13 pgs.

International Search Report and Written Opinion received for PCT Serial No. PCT/IB2022/051293 on Apr. 8, 2022, 16 pgs.

International Search Report and Written Opinion received for PCT Serial No. PCT/IB2022/051321 on Jun. 8, 2022, 16 pgs.

International Search Report and Written Opinion received for PCT Serial No. PCT/IB2022/051328 on Jun. 13, 2022, 16 pgs.

International Search Report and Written Opinion received for PCT Serial No. PCT/IB2022/051279 on Jun. 13, 2022, 15 pgs.

International Search Report and Written Opinion received for PCT Serial No. PCT/IB2022/051244 on Jun. 7, 2022, 13 pgs.

Japanese Search Report received for JP Application No. 2023-548890, 1 pg.

Chinese Search Report received for CN Application No. 2022800154549, 1 pg.

* cited by examiner

FIG. 1A
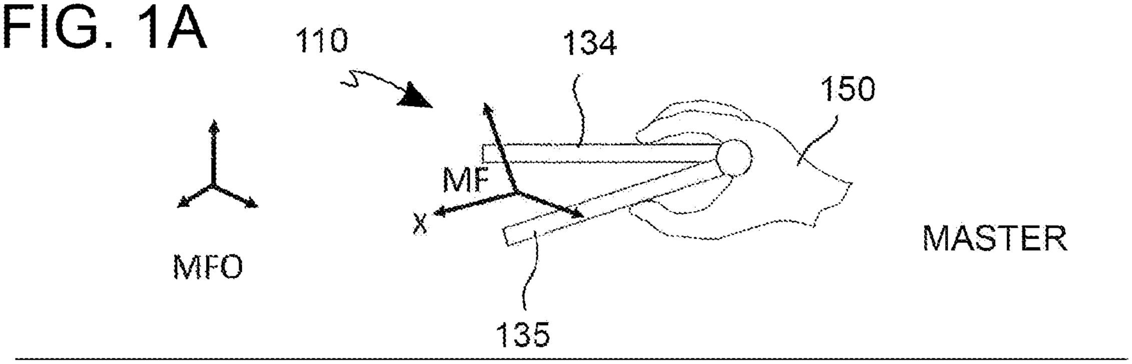
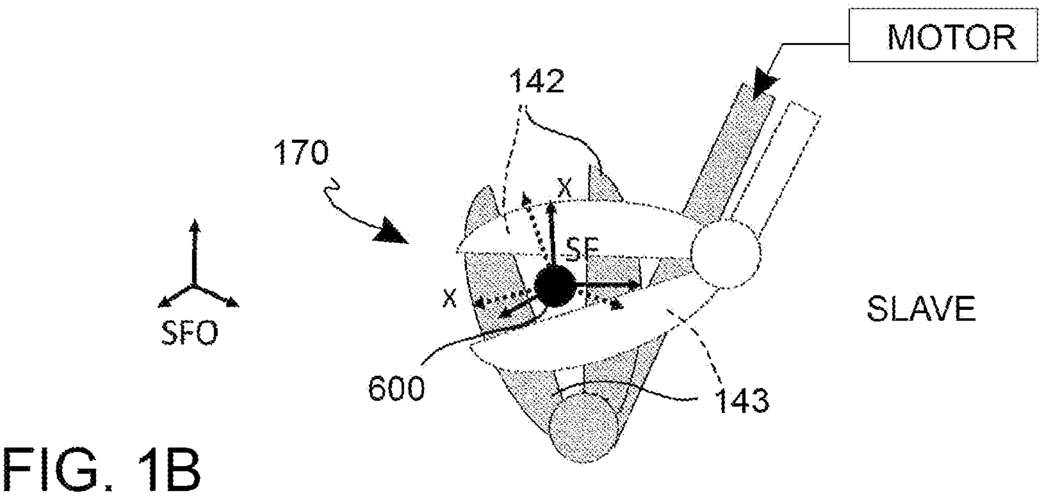
FIG. 1B
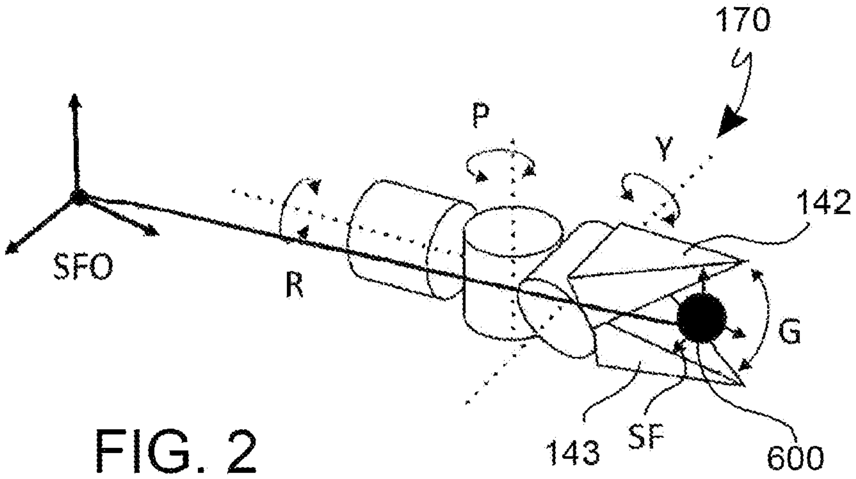
FIG. 2

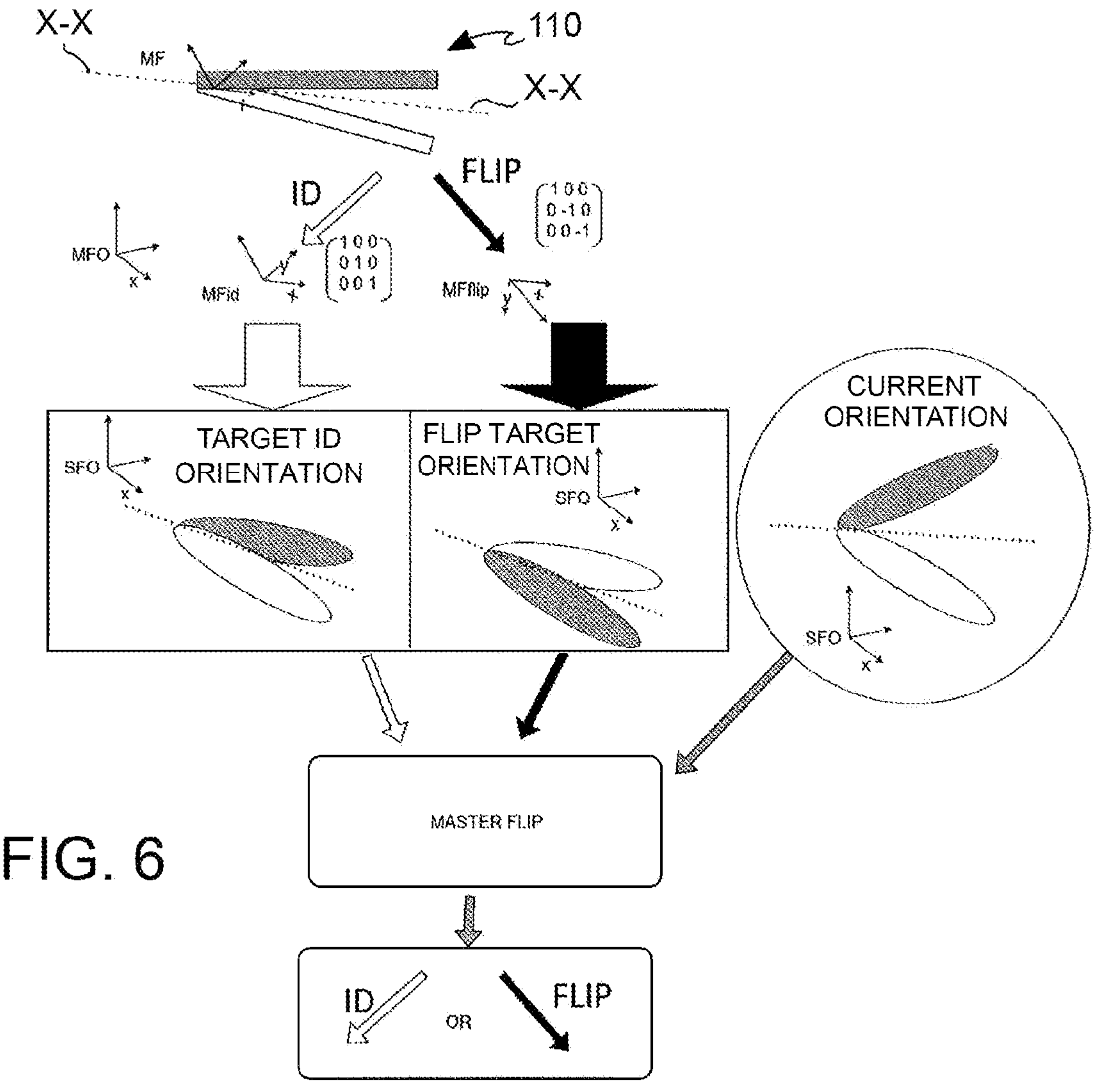
FIG. 6
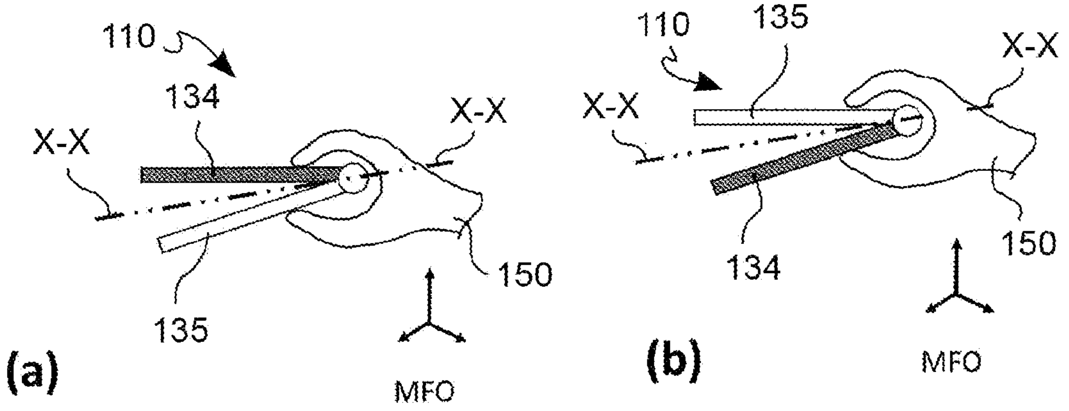
FIG. 6bis

METHOD FOR CONTROLLING A ROBOTIC SYSTEM FOR MEDICAL OR SURGICAL TELEOPERATION, HAVING A MECHANICALLY UNCONSTRAINED MASTER DEVICE BEING MOVABLE BY AN OPERATOR, WITH CONTROL OF LOCAL REFERENCE COORDINATE FRAMES AND ROBOTIC SYSTEM USING THE METHOD

CROSS-REFERENCE TO RELATED APPLICATIONS

The present application is a National Stage Filing of PCT International Application No. PCT/IB2022/051244 filed on Feb. 14, 2022, which claims priority to Italian Patent Application No. 102021000003479, filed on Feb. 16, 2021, which is incorporated herein by reference in its entirety.

TECHNOLOGICAL BACKGROUND OF THE INVENTION

Field of Application

The present invention relates to a method and system for controlling a robotic system for medical or surgical teleoperation.

In particular, the invention relates to a method and system for initiating a teleoperation carried out by means of a robotic system for master-slave type surgical teleoperation, having a master device which is mechanically unconstrained and movable by an operator.

Description of the Prior Art

In the field of master-slave robotic systems for medical or surgical teleoperation, master consoles are known with a mechanically constrained and motorized leg which acts as a "master controller" device.

In such cases, when exiting the teleoperation state, the orientation of the master devices is locked and kept constantly aligned with the slave devices; it can also occur that the master device is moved by motors so as to ensure the complete correspondence of the orientation of the master device with that of the slave device.

If this alignment in orientation between master and slave is not performed, the control of the slave would be hardly intuitive and not ergonomic.

An example of a master-slave robotic system having a master device constrained to a console, which necessarily imposes a finite ability to move the master device, is shown for example in document US-2020-0179068.

Otherwise, solutions have recently emerged with master devices which are not mechanically constrained to the "master controller" station of the robotic system, i.e., "mechanically ungrounded" or "mechanically unconstrained" or "hand-held" devices, or devices of the type as shown for example in documents WO-2019-220407, WO-2019-220408, WO-2019-220409 on behalf of the same Applicant, as well as the type as shown for example in document U.S. Pat. No. 8,521,331.

In such solutions, the problem of how to ensure teleoperation initiation procedures, and in particular of alignment between master device and slave device, remains unsolved, in the absence of a mechanical constraint with a master console and of an enslavement ensured by the motors of such a console.

Therefore, in the technical field considered, there is a strong need to effectively perform master-slave alignment procedures and checks on teleoperation initiation, which is not easy (in the absence of mechanical constraint with the master console) and, on the other hand, it is absolutely necessary, and must be carried out so as to meet the very stringent safety requirements which are imposed in the field of teleoperated surgery or microsurgery by means of robotic systems, and requirement of being easy-to-use, requirements which are considered very important by each surgeon.

SUMMARY OF THE INVENTION

It is the object of the present invention to provide a method for controlling a robotic system for medical or surgical teleoperation, which allows at least partially overcoming the drawbacks claimed above with reference to the prior art, and responding to the aforementioned needs particularly felt in the technical field considered.

It is also an object of the present invention to provide a robotic system for medical or surgical teleoperation, controlled by the method, which allows at least partially overcoming the drawbacks claimed above with reference to the prior art, and responding to the aforementioned needs particularly felt in the technical field considered.

By virtue of the proposed solutions, it is possible to achieve a satisfactory level of alignment between at least one unconstrained master device and at least one enslavable surgical instrument (of a slave device), safely and reliably, without for this reason imposing a predetermined movement of the master device and/or maintaining a certain acceptable level of control and intuitiveness for the operator.

BRIEF DESCRIPTION OF THE DRAWINGS

Further features and advantages of the system and method according to the invention will become apparent from the following description of preferred embodiments, given by way of indicative, non-limiting examples, with reference to the accompanying drawings, in which:

FIGS. 1A and 1B show an example of interaction between master device and slave device included in a method embodiment;

FIG. 2 diagrammatically shows a slave surgical instrument, according to an embodiment, as well as some steps of a method according to a possible operating mode;

FIG. 6 diagrammatically shows some steps included in a method embodiment, according to a possible operating mode;

FIG. 6*bis* diagrammatically shows some steps included in a method embodiment, according to a possible operating mode;

DETAILED DESCRIPTION

Figure 3:
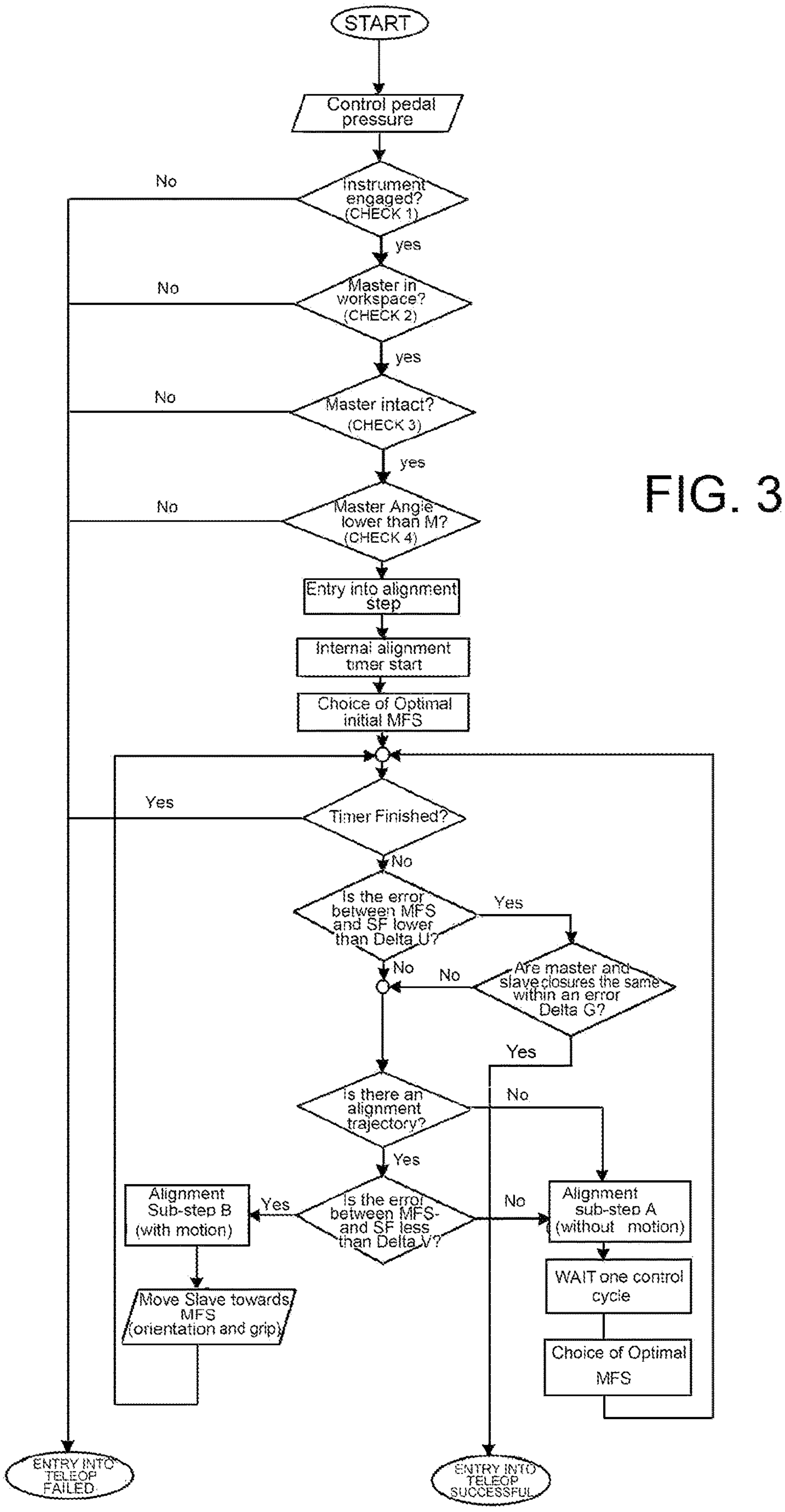
FIG. 3 is a flowchart showing a method embodiment, according to a possible operating mode.
Figure 4:
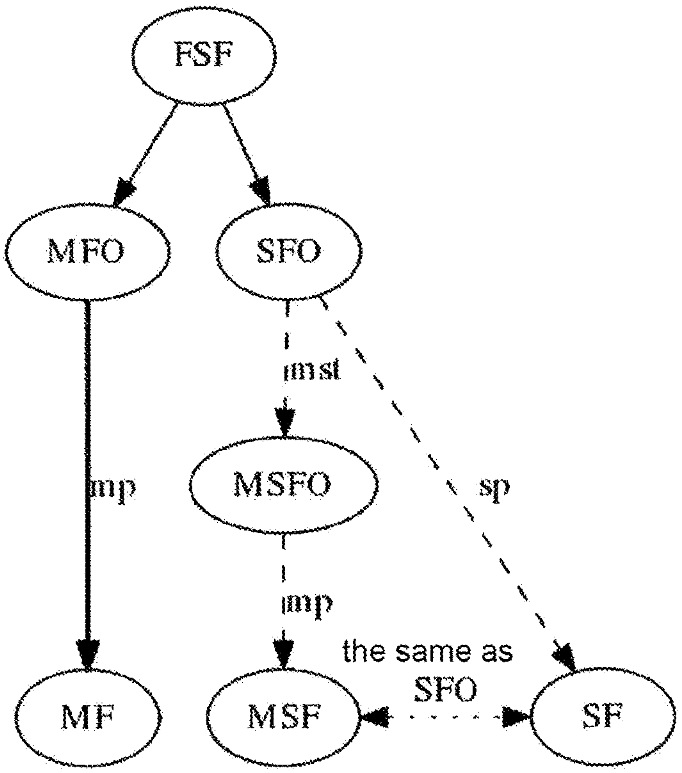
FIG. 4 diagrammatically shows reference frames used in a method embodiment, and transformations between the aforesaid reference frames.
Figure 5:
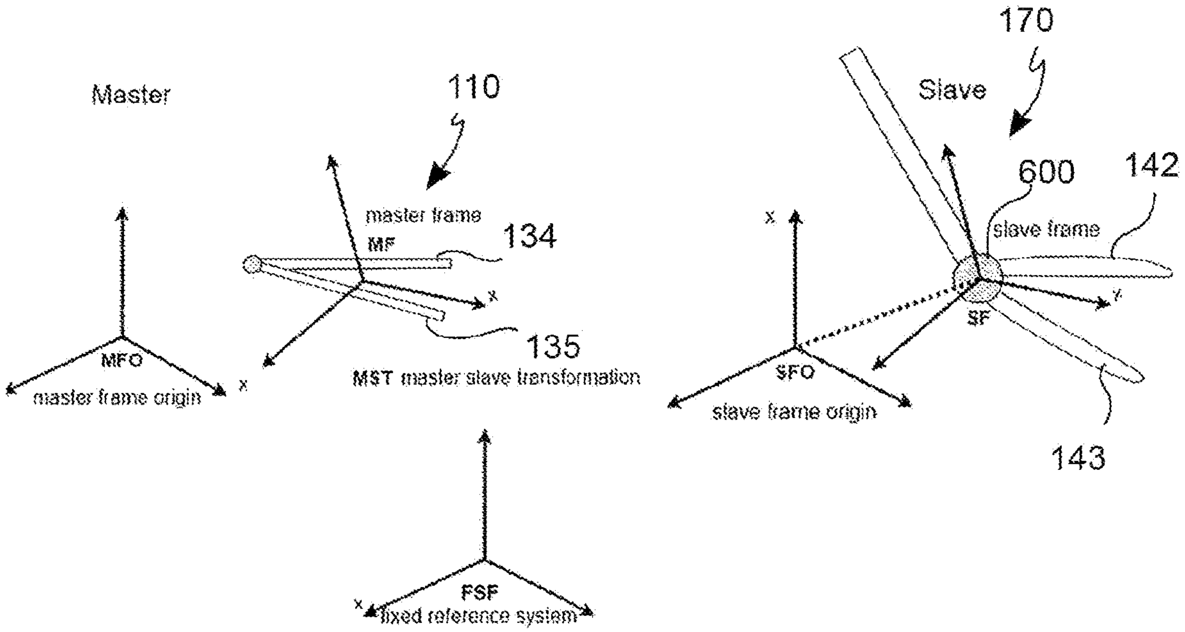
FIG. 5 further shows, diagrammatically, the reference frames mentioned in FIG. 4, and the transformations between the aforesaid reference frames, according to an implementation option.

With reference to FIGS. 1-10, a method for controlling a robotic system for medical or surgical teleoperation is described.

The aforesaid robotic system comprises at least one master device, which is hand-held, mechanically unconstrained and adapted to be moved by an operator, and at least one slave device comprising a surgical instrument adapted to be controlled by the master device. The master device is functionally symmetrical with respect to a predeterminable single, longitudinal axis (X) of the master device.

The method comprises the steps of detecting a local reference frame MF of the master device and its longitudinal axis X, with respect to a main reference frame MFO of the master device workspace; then, defining a plurality of local reference frames which are functionally equivalent to the detected local reference frame, in which such local reference frames are rotated by a respective angle about said longitudinal axis (X) of the master device.

Subsequently, the method provides mapping a corresponding target reference frame in a workspace of the slave device for each of the aforesaid local reference frames of the master device of the aforesaid plurality of local reference frames, functionally equivalent to the local reference frame detected.

Finally, the method comprises the step of selecting an operating reference frame, among the aforesaid plurality of local reference frames functionally equivalent to the local reference frame detected, according to criteria for optimization of the trajectory of the slave device.

According to a method embodiment, the step of detecting further comprises detecting an orientation MF of the longitudinal axis X of the master device; the step of mapping further comprises mapping a corresponding target orientation MFS, in the workspace of the slave device; the step of selecting further comprises selecting an operating reference frame such that the associated target pose is optimal, to converge to said corresponding target orientation MFS.

According to an implementation option, the plurality of local reference frames comprises local reference frames integral with the master device.

According to an implementation option, the plurality of local reference frames comprises local reference frames having a component parallel to the longitudinal axis X.

In accordance with a method embodiment, the detecting step comprises detecting also the pose of the master device, wherein the pose comprises position and orientation information.

According to an embodiment, the method is performed in a generic step of alignment between master device and slave device.

According to an embodiment, the method is performed in a condition in which the surgical instrument of the slave device is not yet aligned with the master device.

In accordance with an embodiment, the method is performed during a step of alignment, with motion or without motion, between the master device and the slave device, under a condition in which the surgical instrument of the slave device is not yet aligned with the master device, and in which the slave device is enabled to move so as to align the orientation of the surgical instrument to an orientation of the master device.

In such a case, the method further comprises the steps of: performing one or more alignment checks, based on the orientations of the master and slave devices, as mapped in the workspace of the slave device; then, expressing the orientation of the master device with respect to the selected aforesaid operating reference frame; then, mapping the aforesaid orientation of the master device, expressed with respect to the selected operating reference frame, to the corresponding target orientation in the workspace of the slave device, i.e., establishing a bi-univocal association between the orientation of the master device and the target orientation of the surgical instrument of the slave device; finally, performing the alignment between the slave device and the master device based on the aforesaid target orientation of the slave device, obtained by mapping the orientation of the master device expressed with respect to the selected operating reference frame.

In accordance with a method embodiment, the rotation angle between the different local reference frames are the same, i.e., N local reference frames are provided, rotated there between by an angle equal to $2\pi/N$.

According to an implementation option, the method provides two local reference frames, a first local reference frame (MF-ID) which is integral with the master device and a second local reference frame (MF-FLIP) which is integral with the master device and rotated by 180° with respect to the first local reference frame about the aforesaid longitudinal axis X of the master device. In such a case, the number N of local reference frames is equal to 2.

According to an implementation option, the aforesaid step of defining a first local reference frame (MF-ID) and a second local reference frame (MF-FLIP) comprises: defining the first local reference frame based on the orientation of the detected master device, and associating therewith an identity transformation function ID; defining the second first local reference frame by applying to the first local reference frame a rotation transformation function FLIP expressed by a rotation matrix of 180° with respect to the longitudinal axis X.

In such a case, the aforesaid step of selecting an operating reference frame comprises selecting a function to be applied to the reference frame, among the aforesaid identity function ID and rotation function FLIP.

In accordance with a method embodiment, the master device has an axial symmetry with respect to the aforesaid longitudinal axis X, and the robotic system does not require alignment with respect to the longitudinal axis X, and thus enables the entry into a teleoperation step and/or operates in the teleoperation step for any rotation of the master device about the longitudinal axis X.

According to a method embodiment, the master device is geometrically symmetrical with respect to the aforesaid longitudinal axis X.

According to a method embodiment, the slave device (and in particular the control point of the slave device) is movable with respect to an axis of the slave device. Such a slave device axis is in relation to the aforesaid longitudinal axis of the master device X according to a predefined correlation.

According to a method embodiment, the slave device (and in particular the surgical instrument of the slave device) is geometrically and/or functionally symmetrical, with respect to the aforesaid axis of the slave device.

According to a method embodiment, the method is used for initiating and/or preparing and/or conducting a teleoperation carried out by the robotic system for medical or surgical teleoperation.

In accordance with an embodiment, during the teleoperation step, in the presence of a rotation movement about the longitudinal axis X, due to the manipulation by the operator, which occurs in a short time, below a predetermined time threshold, the method comprises switching the operating reference frame, from one to the other of the aforesaid local operating reference frames.

According to another embodiment, still referred to the case in which, during the teleoperation step, in the presence of a rotation movement about the longitudinal axis X, due to the manipulation by the operator, which occurs in a short time, below a predetermined time threshold, the method comprises decoupling the enslaved movements of the slave, with reference only to the movements enslaved to those controlled by the longitudinal axis X of the master, until the rolling velocity of the master falls below the aforesaid time threshold.

According to an embodiment, during a phase of limited teleoperation and/or a phase of suspended teleoperation, in which the slave device is enslaved to the master device only for some of the controllable degrees of freedom, the method includes re-evaluating which of the plurality of local operating reference frames to use for the calculation of the target orientation of the master device, in the presence of a rotation movement about the longitudinal axis X, due to the manipulation by the operator, which occurs in a short time, below a predetermined time threshold.

According to an implementation option of the method, the aforesaid rotation movement about the longitudinal axis X, due to the manipulation by the operator, corresponds to a 180° rotation.

According to an embodiment, the aforesaid step of selecting an operating reference frame is performed based on one or more predefined selection criteria, based on the results of the alignment checks.

According to various possible implementation options of such an embodiment, the aforesaid one or more selection criteria are based on values of absolute and/or mutual orientation of the master and slave devices and/or of orientation difference between the master device and the slave device, and/or further comprise verifying other conditions based on the internal and/or external state of the robotic system and/or comprise criteria related to patient safety.

In accordance with a method embodiment, in which the slave device comprises joints adapted to allow rotations and/or movements with respect to one or more degrees of freedom, the aforesaid one or more selection criteria comprise:

- calculating a first distance between the orientations and/or positions of the joints of the slave device and the target orientation of the master device, mapped in the workspace of the slave device, expressed with respect to said first local reference frame;
- calculating a second distance between the orientations and/or positions of the joints of the slave device and the target orientation of the master device, mapped in the workspace of the slave device, expressed with respect to said second local reference frame;
- selecting the first local reference frame or the second reference frame of the master device depending on whether the first distance or the second distance is shorter, respectively.

According to an implementation option, the aforesaid step of selecting comprises selecting the local reference frame which minimizes a weighted function of the distance between the orientations and/or positions of the joints of the slave device and the target orientation of the master device, mapped in the workspace of the slave device.

It should be noted that the target pose and/or target reference frame in the slave space has predefined associated positions and/or orientations of the slave joints.

Optionally, such an association is a unique association.

Optionally, the aforesaid joints are only rotating.

According to a method embodiment, the aforesaid one or more selection criteria comprise selecting the local reference frame which determines a resulting pose and/or orientation of the master device, mapped in the workspace of the slave device, such as to minimize the axis-angle error with respect to the reference frame associated with the slave device in the workspace of the slave device.

According to another method embodiment, the aforesaid one or more selection criteria comprise selecting the local reference frame which determines a resulting pose and/or orientation of the master device, mapped in the workspace of the slave device, such as to maximize the distance from the predefined limits of the workspace of the slave device.

According to a method embodiment, the aforesaid one or more selection criteria comprise selecting the local reference frame which determines a resulting pose and/or orientation of the master device, mapped in the workspace of the slave device, such that the trajectory necessary for the slave device to converge towards the aforesaid resulting pose and/or orientation of the master device is the shortest in terms of angular distance traveled and/or necessary alignment time and/or optimizes criteria related to patient safety.

According to an implementation option, the aforesaid trajectory necessary for the slave device to converge towards the resulting pose and/or orientation of the master device takes into account any obstructions and/or critical areas close to the slave device.

In accordance with a method embodiment, the alignment step includes a plurality of control cycles, and the step of selecting the local reference frame is carried out at each of the aforesaid control cycles of the alignment step, or is carried out only at the beginning of the alignment step.

According to another method embodiment, the alignment step comprises a sub-step of alignment without motion, in which the surgical instrument of the slave device is not enabled to move, and a sub-step of alignment with motion, in which the surgical instrument of the slave device is enabled to move, and the step of selecting the local reference frame is carried out only during the sub-step of alignment without motion.

In accordance with a method embodiment, after the conclusion of the alignment step, the teleoperation step is conducted by expressing the current orientation of the target device, and thus the enslaved orientation of the slave device, based on the operating reference frame selected during the alignment step.

According to another implementation option, the last transformation function selected during the alignment step is used during the entire duration of the subsequent teleoperation.

According to an implementation option, the aforesaid predeterminable longitudinal axis X is an axis defined by the intersection of two symmetry planes of the master device orthogonal to each other.

According to another implementation option, the aforesaid axis of functional symmetry of the slave device is also a geometric axis of symmetry of the slave device, i.e., a symmetrical axis with respect to two slave planes of symmetry.

Another method for initiating and/or preparing a teleoperation carried out by a robotic system for medical or surgical teleoperation, according to a further aspect of the present invention, is now described. Such a robotic system comprises at least one master device, which is hand-held, mechanically unconstrained and adapted to be moved by an operator, and at least one slave device comprising a microsurgical instrument adapted to be controlled by the master device. The body of the master device is ungrounded and is intended to be hand-held by the surgeon during the teleoperation. The master device can be wired for data connection with a portion of the robotic system.

The robotic system further comprises teleoperation preparation first control means. For example, said teleoperation preparation first control means comprise a man-machine interface which allows the operator to communicate the intention to enter into teleoperation to the robot.

The method comprises the steps of initiating a teleoperation preparation step by operating the aforesaid teleoperation preparation first control means; then performing an alignment step between master device and slave device, in which the slave device is enabled to move so as to align the orientation of the surgical instrument to an orientation of the master device; then entering teleoperation after the aforesaid alignment step between master device and slave device has been completed.

During the preparation step and before the alignment step, the method includes carrying out one or more first checks for entering the alignment step, and enabling the start of the alignment step only if all the one or more first checks are successfully passed.

Furthermore, before entering the teleoperation step, the method includes carrying out one or more second checks for enabling the alignment step, and enabling the entry into teleoperation only if all the one or more second checks are successfully passed.

According to a method embodiment, the alignment step comprises a sub-step of alignment without motion, in which the surgical instrument of the slave device is not enabled to move, and a sub-step of alignment with motion, in which the surgical instrument of the slave device is enabled to move.

In this case, the method includes carrying out alignment actions adapted to obtain the alignment of the slave device with respect to the master device, and further includes carrying out one or more third checks adapted to check transitions between the aforesaid sub-steps of alignment with motion and alignment without motion.

According to an implementation option, the above sub-steps of alignment with motion and without motion follow one another in cycles.

In such a case, at the end of each cycle, the method includes checking the outcome of the first checks, and remaining in the alignment step if all the first checks provide a positive result, and exiting the alignment step to return to the preparation step if at least one of the first checks does not provide a positive result; and further checking the outcome of the second checks, and entering the teleoperation step if all the second checks provide a positive result.

In accordance with various possible embodiments of the method, the aforesaid first checks comprise one or more of the following checks:

- check of correct grip of the master device; and/or
- check of acceptability of the position of the master device; and/or
- check of structural integrity of the master device; and/or
- check of the signal quality of the master device; and/or
- checking that the microsurgical instrument is correctly installed on the robotic device.

In accordance with a method embodiment, in which the master device has a degree of freedom of relative movement, the aforesaid check of correct grip of the master device comprises verifying that the degree of freedom of relative movement has exceeded a definable threshold value defined as a resting position.

According to an implementation option, the aforesaid degree of freedom of relative movement is a degree of freedom of opening/closure, and the verifying step comprises verifying that the aforesaid degree of freedom of opening/closure is slightly closed with an opening angle below an opening angle threshold.

According to another implementation option, the aforesaid degree of freedom of relative movement is a degree of freedom of linear displacement, and the verifying step comprises verifying that the linear displacement is an approaching/distancing linear displacement beyond a certain approaching/distancing threshold.

According to another implementation option, the aforesaid degree of freedom of relative movement is a degree of freedom of twist, and the verifying step comprises verifying that the twist is above a certain twist threshold.

In accordance with a method embodiment, in which the master device comprises a contact sensor, for example a capacitive sensor and/or a pressure sensor, the aforesaid check of correct grip of the master device comprises processing information detected by the contact sensor, for example so as to determine if the master device is in contact with the user.

According to a method embodiment, the aforesaid check of the acceptability of the position of the master device comprises verifying that the master device is within a predefined or predeterminable workspace region, for example a spatial region determined by a tracking system.

According to another method embodiment, the aforesaid check of acceptability of the position of the master device comprises verifying that the master device is not in a resting configuration, in which such a resting configuration corresponds for example to a position, and preferably also orientation and/or opening/closing level, of the master device in a workspace region adapted to stow the master device when not hand-held.

In accordance with a method embodiment, the aforesaid checks of the signal quality of the master device comprise verifying that the data communications between master device and system are active and functioning and are supported by electrical signals having a quality level and/or signal-to-noise ratio above respective predefined thresholds.

According to an implementation option, the aforesaid checks of the signal quality of the master device comprise verifying that the sensors of the master device are connected and active.

In accordance with a method embodiment, the aforesaid check of structural integrity of the master device comprises verifying one or more predefined constraints, indicative of the structural integrity of the master device, in which such constraints are verifiable based on detections/measurements of the position and/or velocity and/or acceleration of the master device.

According to an implementation option, the aforesaid structural integrity check of the master device comprises verifying that the master device defines a detected orientation corresponding to an expected orientation.

In accordance with various possible embodiments of the method, the aforesaid second checks comprise one or more of the following checks: check of alignment congruence between the orientations of the master device and the slave device, and/or check of congruence of the opening/closing levels of the master device and the slave device.

According to an embodiment, the aforesaid second checks comprise the check of congruence of both the alignment and the opening/closing levels between the master and slave devices.

According to an implementation option, the aforesaid check of alignment congruence comprises verifying that the master device orientation and the slave device orientation are equal within a predefined tolerance represented by an allowed maximum orientation difference threshold between the orientations of the master and slave devices. In other words, such a check of alignment congruence comprises verifying that the difference between the orientations of the master and slave devices is below the aforesaid maximum orientation difference threshold.

According to an implementation option, the aforesaid check of congruence of the opening/closing levels comprises verifying that the grip closure or opening angle of the master device and the grip closure or opening angle of the slave device are equal within a predefined tolerance represented by an allowed maximum grip closure difference threshold between the opening/closing levels of the master and slave devices. In other words, such a check of alignment congruence comprises, in this case, verifying that the difference between the grip closures or opening angles of the master and slave devices is below said maximum difference threshold between the opening/closing levels.

In accordance with various possible embodiments of the method, the aforesaid third checks comprise one or more of the following checks: check of the reachability of the master device orientation by the slave device orientation, and/or check of alignment congruence of the slave device orientation with respect to the master device orientation.

According to an implementation option, passing all the prescribed third checks allows a transition towards the sub-step of alignment with motion, while failing to pass at least one of the third checks does not allow the transition to the sub-step of alignment with motion, when in the sub-step of alignment without motion, or it forces the transition back to the sub-step of alignment without motion, when in the sub-step of alignment with motion.

In accordance with an implementation option, the aforesaid check of orientation reachability comprises verifying that the initial misalignment between the master device orientation and the kinematic orientation of the surgical instrument of the slave device is less than a master-slave initial misalignment threshold value.

According to another implementation option, the aforesaid check of orientation reachability comprises verifying that a possible alignment trajectory exists.

According to an embodiment, the aforesaid alignment congruence check comprises verifying that the master device orientation and the slave device orientation are equal within a predefined tolerance represented by a maximum orientation difference threshold dV allowed between the orientations of the master and slave devices. In other words, this means verifying that the difference between the orientations of the master and slave devices f(RPYs−RPYm) is below the aforesaid maximum orientation difference threshold dV. Such a parameter dV can correspond to the parameter DELTA V mentioned below.

In accordance with a method embodiment, the alignment congruence check, carried out as part of the aforesaid second checks or as part of the aforesaid third checks, is verified for each degree of freedom of orientation of the slave device. Such a feature will be disclosed in more detail below with reference to “Euler angles”.

In accordance with another method embodiment, the alignment congruence check, carried out as part of the aforesaid second checks or as part of the aforesaid third checks, is verified as a single overall absolute value.

According to an implementation option, the aforesaid maximum orientation difference threshold dV depends on the orientation of the slave device and/or varies based on the orientation of the micro-surgical instrument of the slave device inside the workspace thereof.

According to other possible implementation options, the aforesaid maximum orientation difference threshold dV depends on other parameters.

According to an implementation option, the aforesaid maximum orientation difference threshold dV is verified by means of a decomposition into two sub-rotations, and in which a first error of the first sub-rotation and a second error of the second sub-rotation are verified, with respect to respective thresholds.

For example, in such an implementation option, a “Twist & Swing” calculation method is used, in which, having defined a main direction of the slave device and a main direction of the master device, which are both integral with the main dimensions of the related devices, the first orientation error, or swing error, is defined as the angular error between the main directions thereof, while the second error, or twist error, is defined as the angular distance between the orientations of the master and slave devices, assuming that the first error has been compensated for.

According to another implementation option, the distance between the orientations of the master and slave devices is calculated by a “Quaternion Distance” calculation method.

According to an implementation option, the distances between the orientations of the master and slave devices are calculated using a current threshold calculation method, allowing the transition to the alignment sub-step with a movement on independent axes only for the axes in which the alignment is verified within the respective threshold, or allowing the transition to the alignment sub-step with a movement of all axes only when the alignment is verified for all the axes within the respective threshold.

According to an implementation option, the aforesaid orientation alignment checks are successfully passed for an alignment of 0° or for an alignment rotated by 180° about a longitudinal axis which is definable by the body of the master device, within a misalignment range, preferably only if some of the orientation checks are successfully passed; preferably the master device body is geometrically and/or functionally symmetric with respect to a definable longitudinal axis and the slave surgical instrument body is preferably functionally symmetric with respect to a definable longitudinal axis.

Such features will be disclosed in more detail below.

According to an implementation option, the method also includes verifying that the alignment movement of the control point of the slave device exclusively performs pure rotation movements.

In accordance with a method embodiment, the aforesaid alignment actions comprise one or more actions aimed at obtaining the following behaviors:

constant and/or limited alignment velocity;

velocity of motion inversely proportional to the norm of the vector of the misalignment value or orientation difference;

tracking trajectory of the slave device in accordance with a predefined alignment motion strategy.

According to an implementation option, the velocity of motion of the slave device while aligning the micro-surgical instrument to the master device is below an alignment velocity threshold.

According to another implementation option of the method, the instantaneous angular velocity of the motion alignment trajectory of the slave device is inversely proportional to the norm of the vector of the misalignment threshold value dV.

According to another implementation option of the method, the instantaneous angular velocity of the motion alignment trajectory of the slave device is directly proportional to the time of permanence in the alignment step.

According to another implementation option of the method, the tracking motion of the slave device, from an initial orientation RPYs1 to a final orientation RPYs2, corresponding to the master device orientation, follows a trajectory adapted to monotonically reduce the distance between the two orientations.

In accordance with an embodiment, the method comprises the further step of establishing a maximum permanence time for the sub-steps of alignment with motion and without motion, and of exiting one of the aforesaid sub-steps when the predetermined maximum permanence time is exceeded.

According to a method embodiment, the aforesaid teleoperation preparation first control means comprise a pedal or a button which can be pressed to initiate the alignment step and kept pressed until the alignment step is completed.

The operator can be for example a surgeon or doctor.

According to an implementation option, the method comprises the further step of verifying at each cycle that the pedal or button is kept pressed, and in which, if the pedal or button is not kept pressed, the method includes determining an exit from the alignment step.

According to another implementation option, the method comprises the further step of verifying that the control pedal is released within a timeout period, for example between 3 and 15 seconds, once the alignment step has been completed and entry in the teleoperation step has occurred successfully.

If the pedal is not released, the teleoperation is interrupted. Thus, the method envisages that the robotic system exit the teleoperation when the operator, once the alignment step is completed, keeps the control pedal, or any other teleoperation control means, pressed for a longer time than said exit time threshold (or timeout period).

In accordance with an embodiment, the method comprises the further step of providing an interface between operator and system, operatively connected to the master device, configured to allow the operator to indicate the intention of the operator to access the teleoperation step and to enter into an alignment condition, and preferably also the intention to remain in such an alignment step until the possible completion thereof.

According to an implementation option, the aforesaid interface is a master command of opening/closure or grip configured to actuate an enslaved degree of freedom of opening/closure or grip of the slave device, when in teleoperation.

According to a method embodiment, in which the aforesaid robotic system for medical or surgical teleoperation comprises two master devices, a right master device and a left master device, and two respective slave devices, a right slave device and a left slave device, the method includes that each of the slave devices performs an alignment process with motion with the respective master device independently with respect to the other slave device, with independent alignment times and with individual entry into teleoperation independent of the entry into teleoperation of the other slave device.

According to an implementation option, the start of the alignment step of the right device is simultaneous to the start of the alignment step of the left device. Thereby, it can also be recognized whether the system comprises two master devices or a single master device.

In the aforesaid cases, an implementation option of the method provides that the aforesaid first checks comprise verifying, based on a check of geometric constraints, that the right master device is gripped in the operator's right hand and that the left master device is gripped in the operator's left hand.

According to an implementation option, the aforesaid geometric constraints comprise detecting the relative positions of the left and right master devices within a workspace.

According to an implementation option, the aforesaid geometric constraints comprise verifying that the detected positions of the right and left master devices are located in the right and left half of a workspace, respectively, either relative to the measurement system or relative to a single master device.

In accordance with a method embodiment, the start of the alignment step between the slave device and the master device is subject to the further constraint that the teleoperation control means are operated and/or pressed and kept operated and/or pressed for a predefined time, in order to avoid an involuntary teleoperation start.

According to a further method embodiment, after the start of the teleoperation further checks are performed on further constraints which must be respected during the teleoperation. In such a case, the method comprises the further step of exiting the teleoperation and/or promoting the exit from teleoperation if the aforesaid further constraints are not respected.

According to an implementation option, the aforesaid constraints comprise verifying that the velocities or accelerations of the master and slave devices are below a certain threshold, for a predefined initial teleoperation period.

According to various possible implementation options of the method, the entry into the alignment step, the permanence in such a step and the success or failure of the entry into the teleoperation step are signaled by appropriate audio/video signals, and/or the permanence in the alignment step is identified by an intermittent sound of frequency between 0.5 and 2 Hz.

In accordance with an implementation option, the method includes that the robotic system exits teleoperation when the operator presses the control pedal again or actuates another teleoperation control means.

In accordance with an embodiment, the method operates on a robotic system for teleoperated surgery.

Again with reference to FIGS. 1-10, a robotic system for medical or surgical teleoperation adapted to be controlled by the aforesaid method for initiating and/or preparing a teleoperation is now described.

Such a system comprises at least one master device 110, which is hand-held, mechanically unconstrained and adapted to be moved by an operator 150, and at least one slave device 740 comprising a surgical instrument (170; 770; 780) adapted to be controlled by the master device 110.

The master device 110 is functionally symmetrical with respect to a predeterminable single, longitudinal axis X of the master device.

The system is configured to carry out the following actions:

detecting a local reference frame MF of the master device and the longitudinal axis X thereof, with respect to a main reference frame MFO of the workspace of the master device;

defining a plurality of local reference frames which are functionally equivalent to the local reference frame detected, in which such local reference frames are rotated by a respective angle about said longitudinal axis X of the master device;

mapping a corresponding target reference frame in a workspace of the slave device for each of the aforesaid local reference frames of master device, functionally equivalent to the local reference frame detected;

selecting an operating reference frame, among the aforesaid plurality of local reference frames functionally equivalent to the local reference frame detected, according to optimization criteria of the trajectory of the slave device.

According to an embodiment, the system comprises a control unit configured to carry out said action of detecting, defining, mapping and selecting.

In accordance with various implementation options, the system is configured to carry out the actions of the control method according to any one of the embodiments of such a method disclosed in the present description.

According to various implementation options, the system is configured to carry out the actions of the method for initiating and/or preparing and/or conducting a teleoperation carried out by the robotic system for teleoperation, according to any one of the embodiments of such a method discloses in the present description.

Another robotic system for medical or surgical teleoperation adapted to be controlled by the aforesaid method for initiating and/or preparing a teleoperation is now described.

Such a system comprises at least one master device, which is hand-held, mechanically unconstrained and adapted to be moved by an operator; and at least one slave device comprising a surgical instrument adapted to be controlled by the master device, so that movements of the slave device referred to one or more of a plurality of N controllable degrees of freedom are controlled by respective movements of the master device, according to a master-slave control architecture.

The system further comprises a control unit operatively connected to both the master device and the slave device, configured to control the system so as to perform a method of initiating and/or preparing a teleoperation according to any of the embodiments previously disclosed.

The control unit is preferably adapted to acquire information on the pose of the master device to transmit operating signals to the surgical instrument of the enslaved slave device. The control unit is preferably comprised in a console.

The robotic system preferably comprises a tracking device, for example magnetic tracking and/or optical tracking, to map the position and orientation of the unconstrained or "flying" master device, in order to check the position and orientation of the surgical instrument of the slave device.

Preferably, there is a scaling relationship between translational movements of the master device and enslaved movements of at least one identifying control point of the surgical instrument of the slave device, in other words, the translations of the control point of the slave surgical instrument are a fraction of the translations of the master (in a range from ⅓ to 1⁄20). As the scaling grows, the ability to reposition or accommodate the master device in the work volume thereof becomes particularly advantageous.

In accordance with an embodiment, the system is a robotic system for teleoperated microsurgery. In such a case, the aforesaid surgical instrument of the slave device is a micro-surgical instrument.

Further details of the method and system according to the invention will be provided below, by way of non-limiting example.

According to an implementation option of the method, the aforesaid second checks comprise verifying that the initial misalignment between the master device orientation and the kinematic orientation of the microsurgical instrument of the slave device is less than a master-slave misalignment threshold value.

In accordance with a method embodiment, the aforesaid misalignment threshold value varies based on the orientation of the microsurgical instrument of the slave device with respect to a predefined direction of the robotic system.

Preferably, the misalignment threshold value for enabling the start of the alignment step depends on the current pose and/or the desired pose of the surgical instrument of the slave device with respect to a predefined direction of the robotic system (for example: the longitudinal direction of a positioning spindle constrained upstream of the slave surgical instrument).

According to a method embodiment, the aforesaid second checks comprise verifying that an initial misalignment measured between the master device orientation and a predefined and known direction of the robotic system constrained to the kinematic architecture is lower than a second master-slave misalignment threshold value.

According to an implementation option, the aforesaid second misalignment threshold value is in the range between 0 and 90 degrees in absolute value.

In a further implementation option, the aforesaid second misalignment threshold value is in the range between 0 and 45 degrees in absolute value.

In accordance with an implementation option, the unconstrained master device body is substantially geometrically symmetrical.

The term "geometrically symmetrical" preferably means that the body of the master device is indistinguishable for an operator when rotated 180° about a definable longitudinal axis.

According to an embodiment, the term "geometrically symmetrical" means that the body of the master device is geometrically symmetrical with respect to a longitudinal axis identified by the intersection of two or more definable planes, and in accordance with such an implementation option, a local longitudinal direction of the master device is defined, given by the intersection of the aforesaid planes. In other words, according to this embodiment, the term "geometrically symmetrical" means that the master device body is geometrically symmetrical according to an "N-fold" symmetry.

According to an embodiment, the term "geometrically symmetrical" means that the master device body is geometrically symmetrical with respect to two orthogonal longitudinal and horizontal planes, and in accordance with such an implementation option, a local longitudinal direction of the master device is defined, given by the intersection of the aforesaid planes of symmetry.

Preferably, the surgical instrument of the slave device is functionally symmetrical. The term "functionally symmetrical" means that the surgical instrument of the slave device does not lose any functionality if it is used rotated by 180° about a defined longitudinal axis (for example the "roll" or "twist" axis passing through a shaft of the slave device), even if from a geometric point of view it may not be symmetrical.

According to an implementation option, the surgical instrument of the slave device is geometrically symmetrical as well.

In accordance with an embodiment, the term "functionally symmetrical" means that the body of the slave surgical instrument is symmetrical with respect to the local longitudinal and horizontal planes thereof, allowing the definition of a slave longitudinal direction.

During the teleoperation step, a pure rotation of the master device, with respect to the longitudinal axis thereof, commands a pure rotation having the same amplitude to the slave device with respect to the longitudinal axis thereof.

According to an embodiment in which there is a symmetry of the master device, the master device allows to be handheld indistinguishably by the operator in two symmetrical positions offset by 180° with respect to the longitudinal axis thereof previously mentioned.

As those skilled in the art will appreciate, such a property of indistinguishability of the grasp of the master device associates two possible target orientations for the slave device with each orientation of the master device, offset from each other by 180° with respect to the longitudinal symmetry axis of the master device. Preferably, only one of the two target orientations is used for tracking by the slave device during the teleoperation.

In accordance with an embodiment, such a choice is made based on the mutual orientation between the master device and the surgical instrument of the slave device and/or other contingent and specific operating conditions, before and/or during the alignment step.

In accordance with a different implementation option, such a property of indistinguishability of the grasp of the master device is also obtained in the case of a non-perfect longitudinal symmetry of the master device, and/or the slave device and/or both.

In accordance with a method embodiment, the alignment step with motion provides limiting the movement velocity of the slave device while aligning the microsurgical instrument to the master device, for example so that the movement of the slave can be understood by the operator and is safe.

In accordance with a method embodiment, the alignment step provides that the slave device exclusively performs rotation movements regarding a portion of the slave device itself.

According to an implementation option, the aforesaid portion of the slave device, which is to be verified for rotational movements, is to be understood as the tip of the slave device.

According to an implementation option, the aforesaid checks are performed on a virtual point of action of the micro-surgical instrument, for example the midpoint between the controlled ends of the slave device.

According to an implementation option, other portions of the slave device, other than the tip and articulated thereto (belonging to the upstream positioning and orientation kinematic chain), can translate, and thus are not subject to the aforesaid verification of exclusive rotational movement.

As already noted, in an embodiment, the master device has a degree of freedom of relative movement called opening/closure. According to an implementation option, such a degree of freedom of opening/closure is associated with the deformation level of the master device or a part thereof. According to another implementation option, such a degree of freedom is associated with the amount of force and/or torque induced by the operator on the master device or a part thereof.

In such a case, according to an implementation option, the aforesaid checks comprise verifying that the opening angle is lower than a certain threshold.

According to an implementation option, the aforesaid opening angle threshold is in the range between 10 and 45 degrees between the rigid parts of the master device, or is a deviation threshold in the range between 5 and 15 degrees with respect to the starting opening angle i.e., resting angle.

According to an embodiment, the aforesaid degree of freedom of opening/closure is identified by a deformation/translation of the master, or by the distance of two points integral with the structure of the master itself.

In an embodiment, the points which determine the degree of opening/closure thereof are the tips of the master device. In such a case, the aforesaid linear opening threshold is in the range between 3 and 20 mm and preferably between 3 and 10 mm.

According to an embodiment, the master device has a sensor set adapted to measure the amount of force or torque applied by the operator on the master or in some parts thereof.

In such a case, the aforesaid first checks comprise verifying that the magnitude of the physical quantities measured on the master or in some parts thereof suggest that such a master device is actually handled by an operator.

In a method embodiment, the aforesaid interface between operator and system consists of the position of the unconstrained master device within a work area.

According to an implementation option, a set of poses of the master device are excluded from such a work area, in which such a device is recognized to be in a resting or stowed condition, or stored in a volume adapted to house the master when not handled.

According to an implementation option, such a resting condition is identified by the presence of the master device in a given spatial region as well as by an orientation and/or an opening/closing level of the master device denoting the stowing thereof. In an embodiment, such a resting condition is uniquely identified by the position of the master device in a given spatial region.

It should be noted that, during the alignment step, the enslavement strategy between master and slave is articulated so as to maximize compliance with the safety constraints related to the patient's anatomy and not necessarily minimizing the movement of the slave device. In an implementation option, the slave device may not follow the shortest angular trajectory during alignment.

According to an embodiment, the method includes that the robotic system exits the alignment step if such a step exceeds a time greater than an alignment time threshold between 2 and 15 seconds, for example.

By way of non-limiting example, further details of a preferred method embodiment, comprising a wide variety of checks and verifications, including those already mentioned above, are given below.

The reference frames mentioned below are shown in FIGS. 1-10 (and in particular in FIG. 5):

"master frame" (MF), or "master reference frame";

"master frame origin" (MFO), or "master reference frame origin";

- "slave frame" (SF), or "slave reference frame";
- "slave frame origin" (SFO), or "slave reference frame origin";
- "fixed reference system" (FRS), or fixed external reference system;
- "master to slave transformation" (MST);
- "master frame in slave workspace" (MFS), or "master reference frame in the slave workspace".

In general terms, without considering the degree of freedom of opening/closure ("grip") of the master device and the enslaved surgical instrument of the slave device:

1) the pose of each master device is uniquely identified with a "master frame" (MF) triple" expressed with respect to a reference frame integral with the tracking system called "master frame origin" (MFO).
2) the pose of the slave device is identified with a "slave frame (SF) triple" with respect to a reference frame integral with the robotic system called "slave frame origin" (SFO).

Therefore, given a fixed reference system (FRS), a "master to slave transformation" (MST) is defined as the transformation which maps MFO-related transformations into SFO-related transformations, and thus the application of MST to the transformation from MF to MFO is defined as "master frame in slave workspace" (MFS).

When the system is in remote operation, the robotic system actuates the slave device so that the "slave frame" SF thereof tracks the "master frame in slave reference system" MFS controlled by the user (without translational scale and offset factors).

Therefore, from the rotational point of view, according to an embodiment, the master and slave devices being perfectly symmetrical with respect to a longitudinal plane thereof, it is indifferent that "slave frame" SF tracks "master frame in slave workspace" MFS calculated as described above or deriving from a pre-rotation of "master frame" MF by 180° around the main dimension of the master device (for example the longitudinal extension of the master device body mechanically unconstrained to the console).

In this context, once the possibility of the robotic system and the intention of the operator to start a teleoperation has been verified, the robotic system performs a preliminary step adapted to:

1. Define which of the two possible "master frame in slave workspace" MFS solutions the slave must track. The selection is performed respecting one of the criteria for minimizing the alignment trajectories which will be described in greater detail below.
2. Define the translational offsets between "master frame in slave workspace" MFS and "slave frame" SF so as to uniquely identify during the teleoperation the relative position of the master device in the slave workspace. These offsets are defined at each entry into teleoperation so that each translational slave movement in teleoperation can only be the result of a master movement which occurred after the entry into teleoperation.
3. Align the "slave frame SF triple" with the "master frame in slave workspace" MFS, or start the teleoperation only when the surgical instrument of the slave device has an orientation compatible with that controlled by the user.
4. If present, reproduce the opening/closure state ("grip") of the master device by means of the opening/closure state ("grip") of the surgical instrument of the slave device.

Further details of a preferred method embodiment, comprising a wide plurality of checks and verifications, comprising those already mentioned, and in which the surgeon checks the transitions between the preparation, start and performance steps of the teleoperation through a control pedal, are shown below.

When the surgeon sits at the master console, the robotic system (hereinafter also referred to as "robot") is not yet in teleoperation.

At this point, the surgeon presses the control pedal and holds it down until the alignment step is complete. According to a preferred implementation option, where the control pedal is released prior to the completion of the alignment step, the robot terminates the alignment step without starting the teleoperation step.

Once the operator's action on the control pedal has been detected, the robot is configured to immediately operate the following checks 1), 2), 3), 4).

1) Verification that the surgical instrument of the slave device has been engaged by the robot's micromanipulator, i.e., that the robot has correctly detected and initialized the surgical instrument. For example, according to an implementation option, the surgical instrument has been put in the correct position, for example in a dedicated "pocket" waiting to be actuated and the robot has prepared the actuating means thereof of the surgical instrument ("ready" state), for example an extension of motor pistons.

Upon passing said verification 1), the robot provides a confirmation signal (for example, green light and acoustic signal).

Preferably subsequently, but also simultaneously, the robot proceeds with the following checks:

2) Verification that the master device is inside a workspace arranged for the same master device.

This can be performed for example by means of a tracking sub-system of the master device, comprised in the robotic system. For example, the robotic system can be provided with a tracking magnetic field generator, integral with the master console.

According to an implementation option, the robotic system is provided with an optical tracking system. For example, the optical tracking system comprises a stereoscopic system of cameras and is capable of uniquely identifying the pose of the master device within a predeterminable workspace.

Pressing the control pedal, the robot processes the information coming from the tracking sub-system to detect the presence, or absence, of the master device within a predeterminable work space.

3) Verification that the master device is structurally intact.

This can be done for example by evaluating that two tracking sensors 134, 135 (for example: magnetometer type sensors and/or optical marker) associable with the master device lie in a plane, by comparing the model of the master device with the current pose of the tracking sensors. For example, such a comparison can indicate that the rods, or arms, of the master device body are or are not deformed. Examples of other integrity checks can be based on measurements of the position and orientation of the rods or arms of the master device.

4) Verification that the surgeon provides the intention to enter into teleoperation to the robot.

This can be done by the surgeon by pressing the rods of the master device towards closure. In such a case, the surgeon's intention to enter into teleoperation is detected by verifying that the opening angle of the rods or arms is less than a predeterminable quantity (DeltaM), for example a fraction of the maximum opening and/or the initial opening of the master device arms, thereby detecting approach the tracking sensors 134, 135 approaching each other.

According to an implementation option, a slight closure of the degree of freedom of opening/closure of the master device corresponds to the quantity capable of detecting the intention to enter into teleoperation.

Alternatively, this can be done by assessing the presence of the masters in an area other than the resting area in which the master is stored.

It should be noted that, if the aforesaid checks 1) and then 2), 3), 4)—which preferably occur in real time, i.e., in a fraction of a second—give a positive result, the robot does not yet enter a teleoperation step, but starts an alignment step in which the slave device is enabled to move (which can be signaled by a respective acoustic or visual signal).

If even one of the aforesaid checks fails, then the robot emits an anomaly warning signal (acoustic and/or video), and it is necessary to release the pedal and then press it again to retry, in other words starting over from the step of conveying the intention to enter into teleoperation.

In an embodiment, the user receives acoustic, video or vibration communication from the masters of the entry into the alignment step as well as the entry into complete teleoperation.

In an embodiment, the user receives information regarding the actions to be taken to pass said first checks after pressing the pedal, such as: keeping the master device in the work area, exercising teleoperation intention by means of closing, moving the master device in an orientation direction to exceed the control threshold.

In the alignment step, there is a mismatch between the movement of the master device, held by the surgeon and which could also temporarily remain stationary, and that of the slave device: in fact, the slave device must recover the misalignment with respect to the master device. In other words, one of the objectives of the alignment step is to make sure that the surgical instrument of the slave device recovers any orientation errors with respect to the master device before proceeding with the teleoperation.

In this step, the movement of the surgical instrument of the slave device is still "intuitive" for the operator, as it respects an appropriate tracking strategy and reacting in a predictable manner to the further movements of the unconstrained master device hand-held by the operator, although not necessarily faithfully reproducing, scaled, the movement of the master device. It should be noted that the tips of the surgical instrument of the slave device could be near the patient in this step, and thus large uncontrolled movements of the slave device must be absolutely avoided. For this reason, during the alignment step, the check point which identifies the slave surgical instrument can only perform purely rotational movements, without ever translating. In other words, by providing that the surgical instrument of the slave device performs only rotations, to achieve alignment, without moving in translation, large uncontrolled movements on the slave side are avoided.

In order to minimize the movement of the slave device during the alignment step, said alignment step can be seen as articulated in two sub-steps: A) alignment without slave motion and B) alignment with slave motion, as explained in more detail below. The transition between the two sub-steps can be continuously evaluated by the robot and can occur in both directions, even repeatedly. Overall, the alignment step ends either with the entry into a master-slave teleoperation state or with failure.

As previously stated, the master device can be geometrically and/or functionally symmetrical and the surgical instrument of the slave device can have at least a functional symmetry.

According to an implementation option, both the master device and the slave surgical instrument are horizontally and longitudinally symmetrical, i.e., for each of the master and slave devices a longitudinal direction (axis of symmetry) given by the intersection of the relative two symmetry planes (biplanar symmetry) is definable.

When the master device is symmetrical, two symmetrical configurations of the master device with respect to the longitudinal axis are indistinguishable by the operator and are functionally and geometrically equivalent. According to such an implementation option, two symmetrical configurations of the slave device with respect to the longitudinal direction thereof are functionally equivalent, and preferably also geometrically equivalent and indistinguishable.

According to such an implementation option, the robotic system pre-processes the spatial orientation of the master device before being transposed into the slave space as a "master frame in slave workspace" MFS. The pre-processing can comprise applying one of the two possible transformation functions to the master pose MF which exploit the properties of symmetry between the master and slave devices, i.e.:

(i) apply the "flip" transformation function, i.e., rotate the master pose by 180° about the axis of longitudinal symmetry thereof, or (ii) apply the "identity" transformation function, i.e., do not change the starting master pose.

Based on the mutual and/or absolute orientation of the master and slave devices and/or other conditions based on the internal and/or external state of the robotic system, the robotic system selects between the "identity" and "flip" functions which to use for the calculation of the target orientation to be used for tracking. The selection is made in accordance with one or more of the criteria described below.

CRITERION FLIP 1)—Among "identity" and "flip", select the transformation function which minimizes a weighted function of the distance between the orientations and/or positions of the joints (for example, joints of the surgical instrument of the slave device, and/or of the micromanipulators of the slave device) of the slave device and those of the joints related to the resulting target pose "master frame in slave workspace" MFS.

CRITERION FLIP 2)—Among "identity" and "flip", select the transformation function the resulting pose "master frame in slave workspace" MFS of which minimizes the axis-angle error with respect to the "slave frame" SF.

CRITERION FLIP 3)—Among "identity" and "flip", select the transformation function the resulting "master frame in slave workspace" MFS of which maximizes the distance from the limits of the slave workspace. This thereby reduces the probability of the operator exiting the workspace during the next teleoperation step.

CRITERION FLIP 4)—Among "identity" and "flip", select the transformation function such that the trajectory necessary for the slave device to converge to the resulting "master frame in slave workspace" MFS is the shortest in terms of the angular distance traveled and/or the necessary alignment time and/or optimizes criteria related to patient safety.

According to an implementation option, such a trajectory could take into account any encumbrance and/or critical areas near the slave device.

According to an implementation option, the robotic system selects the transformation function which best meets one or more selection criteria at each control cycle of the alignment step. According to such an implementation option, the last transformation function selected during the alignment step will be used during the entire duration of the next teleoperation.

According to a different implementation, the selection of the transformation function used occurs only in the initial moments of the alignment step.

According to a different implementation, the selection of the transformation function used is performed only during the alignment step without motion.

According to an implementation option which provides the symmetry of each of the master devices (geometric symmetry) and slave surgical instrument (at least functional symmetry which can also be geometric) with respect to a respective definable longitudinal axis, or a respective definable at least one longitudinal plane, the robot evaluates the spatial orientation of the master device in the slave space ("master frame in slave workspace" MFS) in two possible configurations, i.e., (i) the configuration obtained directly from the pose of the master device, and (ii) the configuration obtained rotating ("flipping") the master device body by 180° about the longitudinal extension direction thereof. The robot then selects the configuration which meets one or more of the following requirements (hereinafter referred to as "MASTERMAP").

MASTERMAP 1)—Select the "Master frame in slave workspace" MFS which minimizes a weighted function of the movement of the joints (for example, joints of the surgical instrument of the slave device, and/or of the micromanipulators of the slave device) of the robotic system. It is thereby possible to minimize the movement of one or more joints of the robotic system during the alignment step, avoiding possible drifts towards the limits of the physical slave workspace.

MASTERMAP 2)—Select the "Master frame in slave workspace" MFS which minimizes the axis-angle error with "slave frame" SF. It is thereby possible to minimize the physical movement of the slave device perceived by the operator during the alignment step.

MASTERMAP 3)—Select the "Master frame in slave workspace" MFS which minimizes the distance between the final "slave frame" SF orientation and the limits of the physical slave workspace. Thereby, the probability that the operator exits the physical workspace imposed by the kinematics of the joints of the robotic system in the next teleoperation step is reduced.

Regardless of the sub-step of the alignment step in progress, at any moment the robot uses the "master frame in slave workspace" MFS which best meets the selection criterion adopted. The "master frame in slave workspace" MFS used in teleoperation will be the last "master frame in slave workspace" MFS selected during the alignment step.

According to a different implementation, the "master frame in slave workspace" MFS is fixed using one of the criteria listed above as soon as the alignment step begins.

According to a different implementation, the "master frame in slave workspace" MFS is fixed using one of the criteria listed above only in a sub-step of the alignment step in which the slave device is not in motion.

The two sub-steps A, B which describe the alignment process are described in more detail below.

The first alignment sub-step A is an "alignment without slave motion" step. Such a sub-step A does not provide any motion of the slave device and does not complete the master-slave alignment.

In this sub-step A, the robot performs further checks, including the following ones.

A1) Verification that the master device has a three-dimensional orientation reachable by the slave device, i.e., that a movement of the slave device to achieve the orientation of the master device is feasible. In other words, the robot verifies that the orientation of the master device identified by "master frame in slave workspace" MFS has a three-dimensional orientation such that there is a trajectory inside the slave workspace which converges to "master frame in slave workspace" MFS. The robot does not necessarily process the shortest alignment path, as it can take into account boundary conditions dictated by the patient's anatomy or other operating conditions, as well as optimization and trajectory safety criteria.

It should be noted that the tip or spout 142, 143 of the surgical instrument of the slave device identified by the "slave frame SF triple" with respect to a "slave frame origin" SFO reference frame refers to a control point belonging to the slave surgical instrument or a virtual point rigidly associated with the slave surgical instrument. The control point must move in this step only for pure rotations, avoiding any translations. This helps to avoid potential catastrophic risks for the patient.

According to different implementation options, the check performed by the software of the robot can be performed by taking the aforesaid tips as the check point(s), or virtual points which do not coincide with the free end of the tip, but, for example, at or around the point of the spout or tip intended to grip the surgical needle with contact.

A2) Verification that the angular distance between the master device identified by "master frame in slave workspace" MFS and the slave device identified by "slave frame" SF, is limited by a quantity DELTA V. Thus, according to an implementation option, an orientation of the tips 142, 143 of the slave surgical instrument which is above a predeterminable tolerance value "DELTA V" is also accepted by the robot. Such a value of "DELTA V" can be predetermined depending on various parameters such as the absolute orientation of the tips of the slave device.

According to different implementation options, the calculation of the value of DELTA V can be obtained using the following calculation methods.

DELTAV1) "Euler angles" calculation method. In this implementation option, the Euler angle vector (MEUL) of the "master frame in slave workspace" MFS is defined with respect to the "slave frame origin" SFO reference frame and the corresponding slave vector (SEUL) of "slave frame" SF thereof related to "slave frame origin" SFO. Therefore DELTA V is also defined as a three-elements vector expressed in an angular unit of measurement. In this case, the verification A2 is passed if:

$$|\mathrm{MEUL}\ i - \mathrm{SEUL}\ i| < \mathrm{DELTA}\ V$$

for each element i of the vector.

For the extraction of the Euler angles, it is possible to use the RPY convention ("roll-pitch-yaw") or any of the other 11 sequences of non-consecutive equal axes contemplated by the already known method of representing Euler angles. A possible choice for DELTAV is between 5° and 15°.

DELTAV2) "Quaternion Distance" calculation method. In this implementation option, the angular distance (EA) between the quaternions (QM and QS) associated, respectively, with the "master frame in slave workspace" MFS and "slave frame" SF frames in the "slave frame origin" SFO reference frame is evaluated, i.e., the scalar quantity of rotation of the relative transformation between "master frame in slave workspace" MFS and "slave frame" SF. Therefore, DELTAV is defined as a scalar expressed in an angular measurement unit. In this case, the verification A2 is passed if:

$$|EA| < \text{DELTA } V.$$

A value of DELTAV between 5° and 15° can be selected.

DELTAV3) "Twist & Swing" calculation method. In this implementation option, the rotation which carries the "slave frame" SF in the "master frame in slave workspace" MFS (i.e., the one necessary for alignment) is seen as a composition of two rotations, i.e.: (i) a twist rotation (RT) of the slave device with respect to the main dimension, i.e., the longitudinal extension, of the tips of the surgical instrument; (ii) a swing rotation (RS) of the slave device with respect to another axis orthogonal to the main dimension, i.e., the longitudinal extension, of the tips of the surgical instrument. Therefore, DELTA V is defined as a two-elements vector which expresses, in an angular measurement unit. the quantity of rotation of the aforesaid rotations RS and RT. In this case, the verification A2 is passed if:

$$|\text{vect}(RT,RS)i| < \text{DELTA } V\, i$$

for both elements i of the vector. The first component can have a greater margin (e.g., from 5° to 30°) while the second a smaller margin (e.g., from 5° to 15°).

According to different implementation options, the quantity DELTA V can be arbitrarily selected large enough to make the condition A2 always true for any "slave frame" SF and "master frame in slave workspace" MFS pair.

According to different implementation options, the quantity DELTA V can be fixed or variable depending on the "slave frame" SF, "master frame in slave workspace" MFS, the selected scale factor ("scaling") or on combinations of these and other internal states of the software of the robotic system.

If the checks A1 and A2 are positively passed, the robot enters the second alignment sub-step, i.e., the "alignment with slave motion" sub-step B.

During such a sub-step, the slave device moves to reach the orientation of the master device. In other words, "slave frame" SF moves to reach "master frame in slave workspace" MFS.

During sub-step B:

(i) if the master device is stationary, the slave device performs a trajectory which leads it to orient itself like the master device;

(ii) if the master device is moving in the meantime, i.e., if the master device moves during sub-step B, then the slave device will move with a trajectory adapted to converge with the current orientation of the "master frame in slave workspace".

Preferably, also during this sub-step B, the aforesaid checks 2), 3), 4) on the master device, previously described, are performed continuously, and the robot exits the alignment step and/or the sub-step B of alignment with motion, when at least one of such checks on the master 2), 3), 4) fails.

According to an implementation option, the robot exits the alignment with motion sub-step B and returns to the alignment without motion sub-step A.

During the alignment with motion sub-step B, the trajectory performed by the slave device respects one or more of the following control strategies:

B1) the instantaneous angular velocity of the alignment trajectory is constant;

B2) the instantaneous angular velocity of the alignment trajectory is limited, i.e., below a certain threshold;

B3) the instantaneous angular velocity of the alignment trajectory is limited, and this limit is directly proportional to the time of permanence in the alignment step;

B4) the instantaneous angular velocity of the alignment trajectory is limited by the smaller of the velocity limits defined above.

B5) the instantaneous angular velocity threshold of the alignment trajectory is inversely proportional to the norm of the vector DELTA V calculated by means of any of the previously mentioned methods, in other words it increases while the master-slave misalignment angle decreases.

The alignment trajectory is appropriately constructed to meet one or more of the following requirements:

B6) the trajectory follows the shortest path;

B7) the trajectory follows the easiest path, determined based on current operating conditions;

B8) the trajectory follows a path dictated by user safety maximization criteria.

During the alignment with motion sub-step B, the closure (grip) of the slave surgical instrument converges with that of the master device with a trajectory meeting one or more requirements B1, B2, B3, B4, B5, B6, B7, B8. During the alignment with motion sub-step B, the conditions A1 and A2 are continuously checked in real time, at periods of the order of small fractions of a second.

If at least one of the aforesaid checks A1-A2 is not passed, then the robot returns to the alignment without motion sub-step A of the slave waiting for both checks A1-A2 to be positive.

If all the aforesaid A1-A2 checks instead give a positive result, then the robot remains in sub-step B until the alignment step is completed.

It should be noted that, also during this sub-step B, the aforesaid checks 2), 3), 4) on the master device, previously described, are performed continuously, and the robot exits the alignment with motion sub-step B, returning to the alignment without motion sub-step A. In this case, it will be possible to return to sub-step B only when the conditions 2) 3) and 4) are also met.

The alignment step is completed when, during sub-step B, the following conditions occur:

COND-TELEOP 1)—the degree of opening/closure (grip) of the master device and the slave device are equivalent (except for an error DeltaGrip);

COND-TELEOP 2)—the orientation error between the master device (i.e., "master frame in slave workspace" MFS) and the slave device ("slave frame" SF) is less than a quantity Delta U called orientation error Delta U. The calculation of the orientation error Delta U can be evaluated by any of the calculation methods already described for the case of DELTA V.

If the above conditions COND-TELEOP 1 and CONF-TELEOP 2 are not reached within a time Timeout A, the robotic system immediately terminates the alignment step, and it will be necessary to release the control pedal before starting a new alignment step.

According to a preferred implementation option, in the transition between the alignment step and the teleoperation step it is determined which of the two possible opposing "master frame in slave workspace" MFS configurations will be used in the remainder of the teleoperation. In addition, the translation offsets of "master frame in slave workspace" MFS are preferably defined such as to allow, at the very first instant of entry into teleoperation, to obtain a relative position of the master device coinciding with the origin of "slave frame" SF with respect to the reference frame "slave frame origin" SFO.

According to a further implementation option, upon the loss of one or more of the above conditions, it follows that the robot exits the alignment with motion sub-step B and returns to the alignment without motion sub-step A. In this case, it will be possible to return to sub-step B only when also the conditions 2) 3) and 4) are met again.

The teleoperation step provides that in a first phase of limited duration the movements are limited in terms of velocity and/or acceleration, so as to avoid movement jerks of the slave device during the transition from the alignment step to the teleoperation step.

According to an implementation option, once the robot enters the teleoperation step, the control pedal must be released within a certain timeout T, for example between 3 and 20 s. If the pedal is not released within such a time, the robotic system exits the teleoperation state, and it will be necessary to release the pedal and restart the alignment sequence.

What is described above refers to the case in which there is only one master device and only one slave device.

In a preferred system embodiment, in which there are two master devices and two slave devices, the control strategy is structured as follows:

both master-slave pairs 1 and 2 must enter the alignment step together (simultaneously);

both master-slave pairs 1 and 2 must enter the teleoperation step together (simultaneously).

Consequently:

(i) if one of the two master-slave pairs does not enter the alignment step (for example, the surgical instrument is not engaged and check 1 fails, or the surgeon has not expressed an intention to operate on one of the masters, and check 4 fails), it is possible to continue with the alignment of only one of the two pairs, and then it is possible to further teleoperate with only the master-slave pair which has passed all the checks;

(ii) if one of the two pairs (for example, the master-slave pair 2) does not enter into teleoperation, but both pairs have already entered the alignment step, the robot waits until both master-slave pairs 1 and 2 are aligned, before entering into teleoperation; this process can last a few seconds.

In this case, if the alignment cannot be reached, teleoperation with a single master-slave pair is not allowed, and the operator must return to the beginning of the entire procedure, i.e., must release the pedal and then press it again.

In a preferred system embodiment, the control strategy is structured as follows:

(COND1) if both master-slave pairs 1 and 2 enter the alignment step, they do so together (simultaneously).

(COND2) if both master-slave pairs 1 and 2 have entered the alignment step, they will eventually enter the teleoperation step together (simultaneously).

Consequently:

(COND1) if one of the two master-slave pairs does not enter the alignment step (for example, the surgical instrument is not engaged and condition 1 fails), or the surgeon has not expressed an intention to operate on one of the master devices, and condition 4 fails), it is possible to continue with the alignment of only one of the two master-slave pairs, which will also be the only one to enter into teleoperation once the alignment step is completed;

(COND2) if only one of the two pairs (for example, the master-slave pair 2) does not meet the alignment condition, but both pairs have previously entered the alignment step, the robot waits until both master-slave pairs 1 and 2 meet the aforesaid condition, before entering into teleoperation.

In this case, if alignment cannot be achieved, teleoperation with a single master-slave pair is not allowed.

If the predefined time is exhausted, the alignment process will fail for both master-slave pairs and the operator must release the pedal before restarting a new teleoperation entry attempt.

According to different implementation options, COND1) can be relaxed, allowing both master-slave pairs to enter the alignment step in a temporally deferred manner (as long as the "advance" pair is still in the alignment step and has not already entered the teleoperation step)

According to different implementation options, COND2) can be relaxed, allowing one master-slave pair to enter into teleoperation while the other is still in the alignment step. In this case, the slave device which enters into teleoperation can move only by rotation or have a limited possibility of translation.

According to an embodiment, each master device is uniquely assigned to a respective slave device, whereby the right master device must be on the right and control the right slave. In this context, in the case of two master-slave pairs, there is an additional necessary condition for the start of the alignment step, which is condition 5) "right-left exchange": in the case of several master-slave pairs, the position of the frame related to the right master in the reference frame "MFO" must be "on the right" with respect to the frame related to the left master. The evaluation of "right" and "left" is done by projecting the coordinates of the master frames along a direction in MFO coinciding with the natural concept of right and left from the operator's point of view. If the masters are "exchanged", when the control pedal is pressed, it is not possible to start the alignment step but the operator is notified, by a message on the screen, to exchange the masters.

According to different implementation options, the condition 5) can be relaxed or extended to the entire alignment step. In the latter case, meeting condition 5) will be added to conditions A1 and A2 for the persistence of the master-slave pair in the alignment with motion sub-step B.

It should be noted that the parameters DELTA V, DELTA U as well as the construction strategies of the trajectories during the alignment step of the two master-slave pairs are in general independent of each other, and may depend on the state of the robotic system as well as the type of surgical instrument engaged.

In an embodiment, DELTA V is greater than Delta U, i.e., the acceptable misalignment threshold is greater in alignment without motion sub-step A with respect to when in the alignment with motion sub-step B. For example: the set of three DELTA V is calculated with a Euler angle method with a value in the range 10°-90°/10°-60°/10°-85° and Delta U is a value calculated with a "Quaternion distance" method in the range 0°-10°.

According to different implementation options, DELTA V, Delta U of the master-slave pairs can depend on the current state of the alignment procedure. For example, the convergence of one of the pairs or the time elapsed since the start of the alignment step can widen the tolerance margins DELTA V and Delta U so as to increase the usability of the robotic system.

In summary, the implementation option disclosed in detail above can be summarized as follows:

the surgeon presses the pedal and keeps it pressed until the end of the alignment procedure;

the system is configured to carry out checks on the following aspects, concerning the state of the robot as well as check(s) on the operator state, observed by means of the state of the master device:

CHECK 1): the slave surgical instrument is engaged with the slave device;

CHECK 2): the master device is inside the prescribed workspace;

CHECK 3): the master device is voluntarily hand-held by the operator (in an implementation option it is verified that it is not completely open, but slightly closed, to express the operator's intention to enter the teleoperation step); this check can further verify that the signal quality of the tracking system of the master device meets appropriate predefined quality criteria;

CHECK 4): the structure of the master device is intact, in the light of one or more structural integrity tests;

CHECK 5) in the event of intention to enter into teleoperation with both instruments (checks from 1 to 4 respected for two master devices), both master devices are hand-held correctly, i.e., voluntarily hand-held by the operator simultaneously.

If all the above-mentioned checks are passed positively, the robotic system provides the user with an audio and/or video confirmation signal.

The alignment step is entered, and in particular a sub-step of "alignment without slave motion". According to an implementation option, in the event of two master devices, each master-slave pair enters sub-step A of the alignment step independently of the other. In said sub-step A:

A1: check if the master has an orientation reachable by the slave;

A2: check that the distance between the orientation of the master device and that of the slave device is less than a quantity DELTA V.

If the above occurs, a sub-step B of "alignment with motion" of the slave is entered, in which the slave device is moved to reach the master device, and in particular the orientation and the degree of opening/closure controlled by the respective master device. If one of the conditions A1 or A2 is missed, the robotic device returns to sub-step A of the alignment step.

During the alignment sub-step B, the slave device moves only by rotations with trajectories which respect control dynamics as described above.

Where there is symmetry of the bodies of the master and slave devices with respect to the respective longitudinal axis/plane, it is possible to control the slave device both with the "master frame in slave workspace" MFS and with the version thereof rotated by 180° with respect to the main dimension, i.e., the longitudinal extension, of the master device. For this reason, in both sub-steps, it can be continuously decided which of the two versions of "master frame in slave workspace" MFS to use based on certain optimization criteria described above.

If during any of the sub-steps, one of the conditions from CHECK2-CHECK4 falls, the robotic system immediately interrupts the alignment step. Other implementation options already described in the document relax this condition.

If after a predefined time the robotic system is still in the alignment step, the alignment step ends without entering into teleoperation. Otherwise, if within a predefined time all the master-slave pairs which have begun the alignment have actually aligned therein (subject to said error Delta U), the robotic system enters into teleoperation.

Entering teleoperation, for each of the master-slave pairs, the used version of "master frame in slave workspace" MFS is frozen and the translational offsets between the master space and the slave space are defined.

According to an implementation option, at the beginning of the teleoperation step, slave accelerations and velocities are limited for a certain initial finite time period.

Once in teleoperation, the control pedal must be released within a certain time, under penalty of forced interruption of the teleoperation. The operator is able to distinguish the presence in the alignment step and the transition to the teleoperation step by means of a change of audio and video interface. According to an implementation option, the robot emits an intermittent sound during the alignment step. Such a sound is concluded with several other sounds, distinguishable from each other, if the entry into teleoperation has been successful or if the alignment step has failed.

In the example shown in FIG. 1, the alignment step is diagrammatically shown in which the slave device 170 is enabled to move in the workspace of the slave 175 to align with the master device 110 (in the example shown, the starting pose of the slave surgical instrument 170 is shown with shading and continuous line and the target pose of the slave surgical instrument 170 which is aligned with the pose of the master device 110 is shown without shading in dashed line), and in which the check point 600 of the slave surgical instrument 170 exclusively performs purely rotational movements to align with the pose of the master device 110.

In the example in FIG. 1, the master device body comprises two rigid parts which are integral with respective sensors or markers 134, 135 constrained in a rotational joint to rotate about a common axis.

In the example shown in FIG. 2, a slave surgical instrument 170 is diagrammatically shown comprising an articulated wrist provided with joints for roll R, pitch P and yaw Y movement, as well as provided with a degree of freedom of opening/closure (or grip G) between the tips 142, 143, in which the check point 600 is enabled to exclusively perform pure rotation movements during the alignment step. The tips 142, 143 are both shown hinged about the yaw axis Y.

The example in FIG. 6 diagrammatically shows the selection of the identity function or the flip function in accordance with what is described above.

In the example shown in FIG. **6*bis*, an unconstrained master device 110 is shown having a body geometrically symmetrical with respect to a longitudinal axis X-X, in which the master device body comprises two rigid parts integral with respective sensors or markers 134, 135 constrained in a rotational joint to rotate about a common axis; in the example shown, the body of the master device 110 is shown hand-held by a surgeon 150** in two configurations (a) and (b) rotated by 180° with respect to each other about the longitudinal axis X-X. The symmetry diagrammatically shown here is of a geometric type both for the master and for the slave, although the slave device and/or the master device may not be geometrically symmetrical, still resulting functionally symmetrical.

As described above, the master device 110 does not necessarily comprise two rigid parts constrained in a rotational joint to rotate about a common axis to control an enslaved degree of opening/closure or grip G, and for example the master device can comprise two rigid parts constrained to translate with respect to each other along a common axis and/or a button and/or a sensorized interface for example comprising a presence or contact sensor to control an enslaved degree of freedom of opening/closure or grip G.

Figure 7:
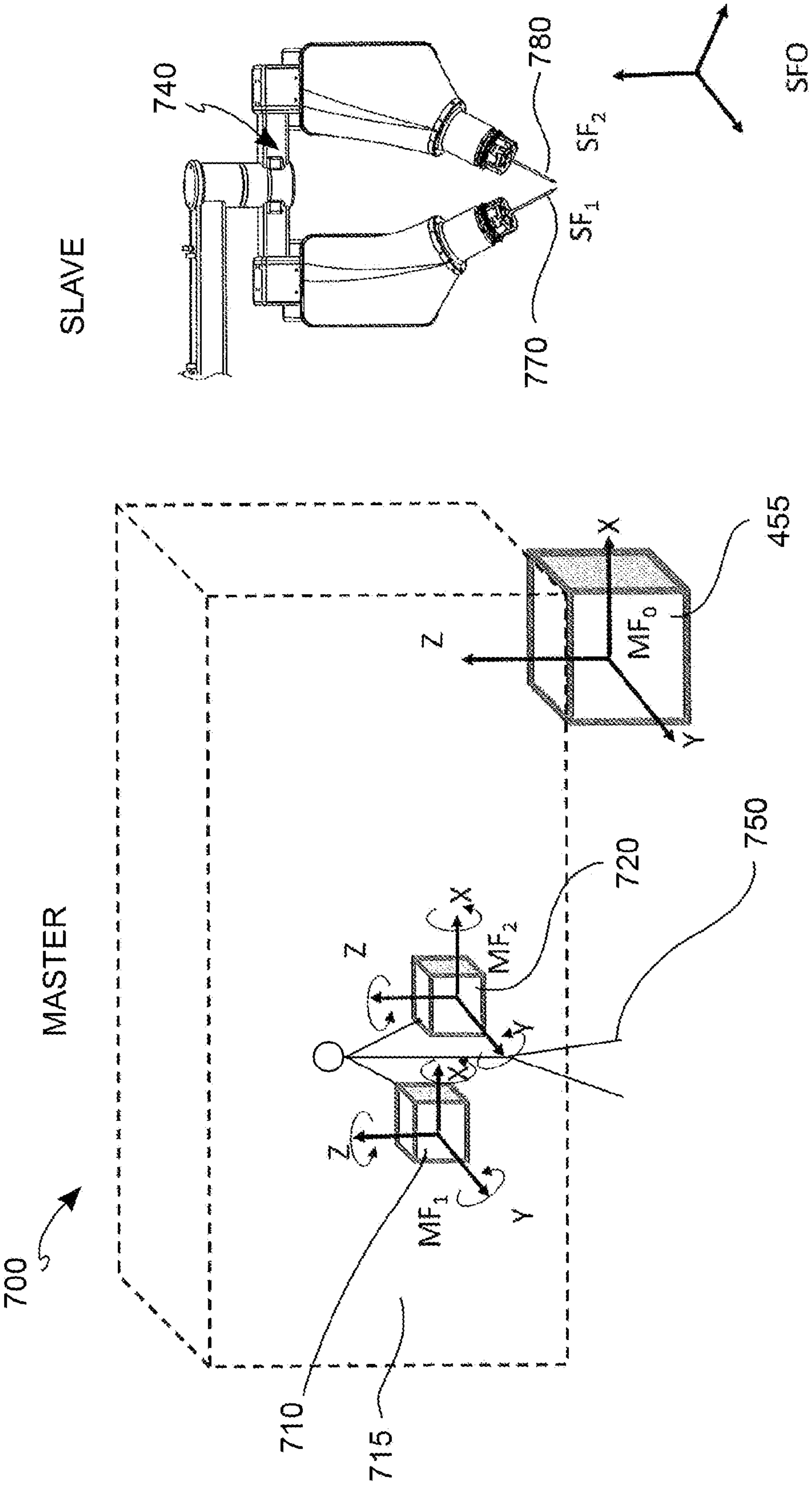
FIG. 7 diagrammatically shows a teleoperated system (or robotic teleoperation system), according to an embodiment.

FIG. 7 shows an embodiment of a teleoperated robotic system 700 in which two master devices 710, 720 held by a surgeon 750 are shown inside a workspace 715 integral with a console 755, and an enslaved slave device 740 comprising two slave surgical instruments 770, 780 respectively enslaved by the two master devices 710, 720.

Figure 8:
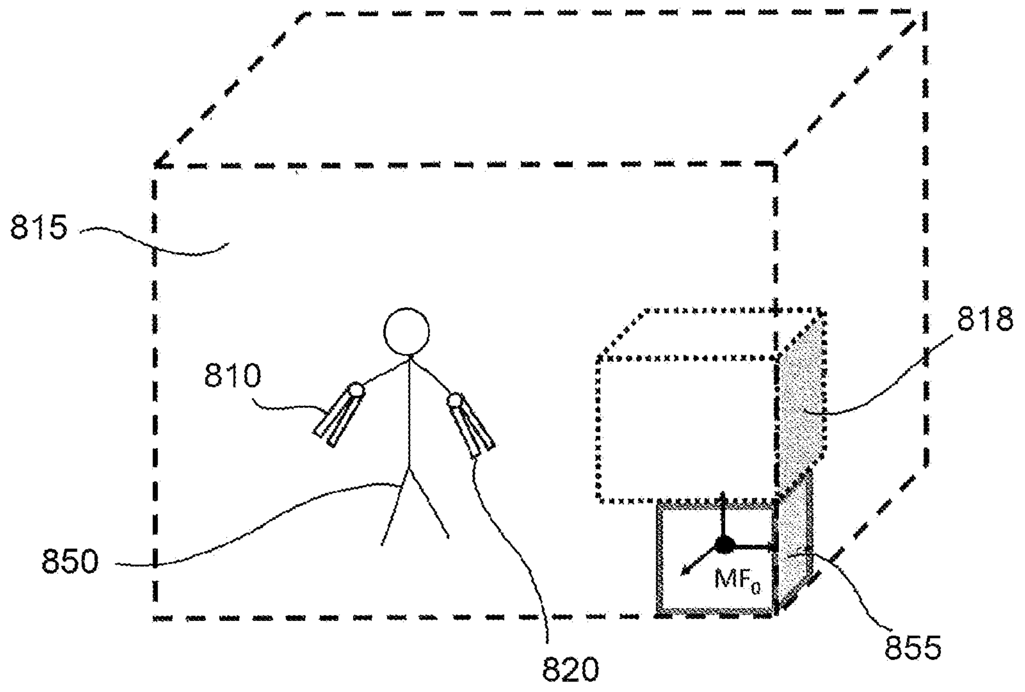
FIG. 8 diagrammatically shows a portion of a teleoperated system (or robotic teleoperation system), according to an embodiment, as well as some steps of a method according to a possible operating mode.

The example shown in FIG. 8 shows a rest or stow region 818 inside the workspace of the master 815 integral with the console 855, in which the unconstrained master devices 810, 820 are shown hand-held by a surgeon 850, and in which the robot can verify that the master devices 810, 820 are not inside the stow region 818.

Figure 9:
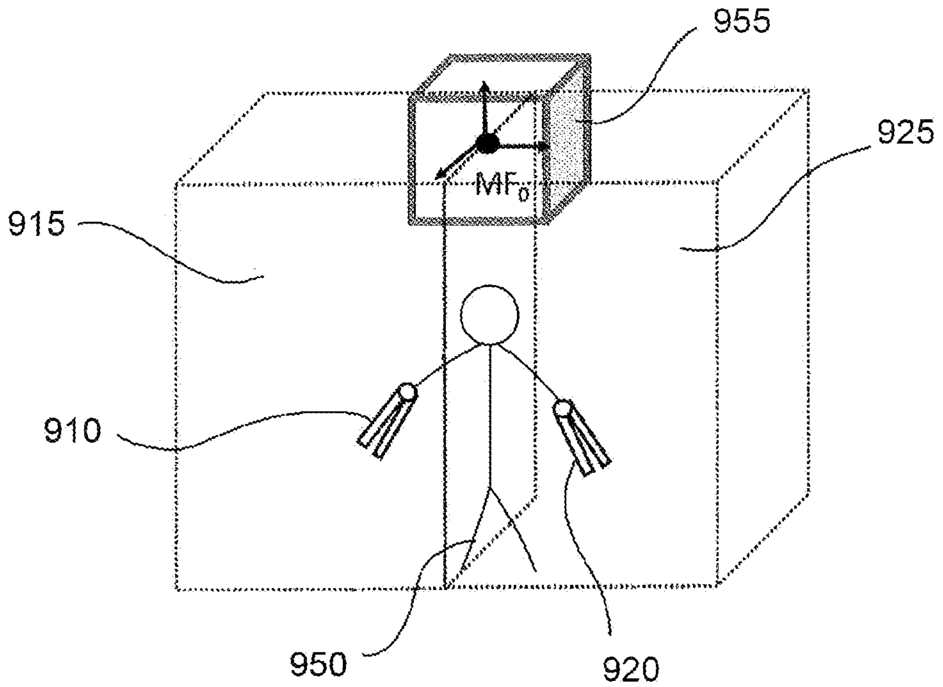
FIG. 9 diagrammatically shows a portion of a teleoperated system (or robotic teleoperation system), according to an embodiment, as well as some steps of a method according to a possible operating mode.

FIG. 9 shows two unconstrained master devices 910, 920 hand-held by a surgeon 950, in which the robot verifies that each master device 910, 920 is within the respective workspace 915, 925 thereof (each right and left workspace 915, 925 is shown integral with the console 955).

Figure 10:
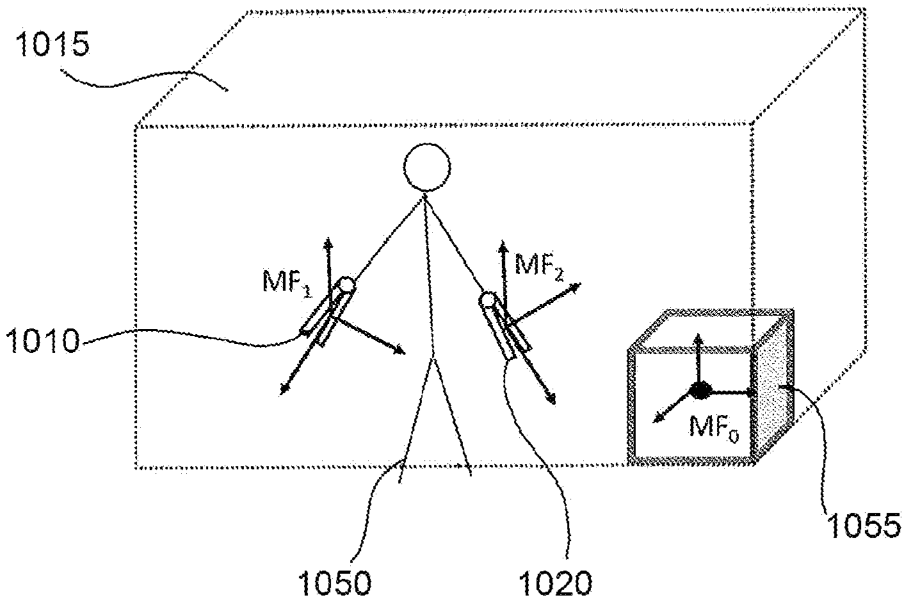
FIG. 10 diagrammatically shows a portion of a teleoperated system (or robotic teleoperation system), according to an embodiment, as well as some steps of a method according to a possible operating mode.

FIG. 10 shows two unconstrained master devices 1010, 1020 held by a surgeon 1050, in which the robot verifies that both master devices 1010, 1020 are inside a workspace 1015 (shown here integral with the console 1055) in a respective spatial relationship.

As can be seen, the objects of the present invention as previously indicated are fully achieved by the method described above by virtue of the features disclosed above in detail.

In fact, the method and system described above make it possible to effectively perform master-slave alignment procedures and checks on teleoperation start, even for mechanically unconstrained master devices.

The procedures and checks performed before and during the alignment, and before the teleoperation, can be articulated in various manners, depending on the needs, and allow meeting a wide range of safety requirements, even very stringent, which are imposed in the field of surgery or microsurgery teleoperated by means of robotic systems.

In order to meet contingent needs, those skilled in the art may make changes and adaptations to the embodiments of the method described above or can replace elements with others which are functionally equivalent, without departing from the scope of the following claims. All the features described above as belonging to a possible embodiment may be implemented irrespective of the other embodiments described.

The invention claimed is:

1. A method for controlling a robotic system for medical or surgical teleoperation, wherein said robotic system comprises at least one master device, which is hand-held, mechanically unconstrained and adapted to be moved by an operator, and at least one slave device comprising a surgical instrument adapted to be controlled by the master device, wherein the master device is functionally symmetrical with respect to a predeterminable single, longitudinal axis of the master device, wherein the method comprises:

detecting a local reference frame of the master device and the longitudinal axis of the master device, with respect to a main reference frame of a workspace of the master device;

defining a plurality of local reference frames which are functionally equivalent to the local reference frame detected, said local reference frames being rotated by a respective angle about said longitudinal axis of the master device;

mapping a corresponding target reference frame in a workspace of the slave device for each of said local reference frames of the master device of said plurality of local reference frames functionally equivalent to the local reference frame detected;

selecting an operating reference frame, among said plurality of local reference frames functionally equivalent to the local reference frame detected, according to criteria for optimization of a trajectory of the slave device.

2. The method according to claim 1, wherein:

the detecting step further comprises detecting an orientation of the longitudinal axis of the master device;

the mapping step further comprises mapping a corresponding target orientation, in the workspace of the slave device;

the selecting step comprises selecting an operating reference frame such that an associated target pose is optimal, to converge to said corresponding target orientation.

3. The method according to claim 1, wherein the method is performed during a generic step of aligning the master device with the slave device, and/or under a condition in which the surgical instrument of the slave device is not yet aligned with the master device.

4. The method according to claim 1, wherein the method is performed during a step of alignment, with motion or without motion, between the master device and the slave device, under a condition in which the surgical instrument of the slave device is not yet aligned to the master device, and wherein the slave device is enabled to move so as to align an orientation of the surgical instrument to an orientation of the master device;

wherein the method further comprises the steps of:

performing one or more alignment checks, based on the orientations of the master and slave devices, as mapped in the workspace of the slave device;

expressing the orientation of the master device with respect to said operating reference frame selected;

mapping said orientation of the master device, expressed with respect to the operating reference frame selected, in the corresponding target orientation in the workspace of the slave device, establishing a one-to-one association between said orientation of the master device and the target orientation of the surgical instrument of the slave device;

performing the alignment between the slave device and the master device based on said target orientation of the slave device, obtained by mapping the orientation of the master device expressed with respect to the operating reference frame selected.

5. The method according to claim 1, wherein the rotation angles between the different local reference frames are the same, where a number N of local reference frames are provided, rotated by an angle of $2\pi/N$ to one another.

6. The method according to claim 5, comprising two local reference frames, a first local reference frame which is integral with the master device and a second local reference frame which is integral with the master device and rotated by 180° with respect to the first local reference frame about said longitudinal axis of the master device.

7. The method according to claim 6, wherein said step of defining a first local reference frame and a second local reference frame comprises:

defining the first local reference frame based on the detected orientation of the master device, and associating an identity transformation function therewith;

defining the second first local reference frame by applying, to the first local reference frame, a rotation transformation function expressed by a rotation matrix of 180° with respect to the longitudinal axis; and wherein said step of selecting an operating reference frame comprises selecting a function to be applied to the reference frame, among said identity transformation function and rotation transformation function.

8. The method according to claim 1, wherein the master device has an axial symmetry with respect to said longitudinal axis, and wherein the robotic system does not require alignment with respect to said longitudinal axis, and enables entry into a teleoperation step and/or operates in the teleoperation step for any rotation of the master device about the longitudinal axis, and/or wherein the master device is geometrically symmetrical with respect to said longitudinal axis.

9. The method according to claim 1, wherein a control point of the slave device, is movable with respect to an axis of the slave device, said slave device axis being in relation with said longitudinal axis of the master device according to a predetermined correlation.

10. The method according to claim 1, wherein the surgical instrument of the slave device is geometrically and/or functionally symmetrical, with respect to said slave device axis.

11. The method according to claim 1, wherein the slave device comprises joints adapted to allow rotations and/or movements with respect to one or more degrees of freedom, and wherein said one or more selection criteria comprise:

calculating a first distance between the orientations and/or positions of the joints of the slave device and the target orientation of the master device, mapped in the workspace of the slave device, expressed with respect to said first local reference frame;

calculating a second distance between the orientations and/or positions of the joints of the slave device and the target orientation of the master device, mapped in the workspace of the slave device, expressed with respect to said second local reference frame;

selecting the first local reference frame or the second reference frame of the master device depending on whether the first distance or the second distance is shorter, respectively, or selecting the local reference frame which minimizes a weighted function of the distance between the orientations and/or positions of the joints of the slave device and the target orientation of the master device, mapped in the workspace of the slave device.

12. The method according to claim 1, wherein said one or more selection criteria comprise:

selecting the local reference frame which determines a resulting pose and/or orientation of the master device, mapped in the workspace of the slave device, to minimize an axis-angle error with respect to the reference frame associated with the slave device in the workspace of the slave device.

13. The method according to claim 1, wherein said one or more selection criteria comprise:

selecting the local reference frame which determines a resulting pose and/or orientation of the master device, mapped in the workspace of the slave device, to maximize a distance from predetermined limits of the workspace of the slave device.

14. The method according to claim 1, wherein said one or more selection criteria comprise:

selecting the local reference frame which determines a resulting pose and/or orientation of the master device, mapped in the workspace of the slave device, such that a trajectory necessary for the slave device to converge towards said resulting pose and/or orientation of the master device is shortest in terms of angular distance traveled and/or necessary alignment time and/or optimizes criteria related to patient safety.

15. The method according to claim 14, wherein said trajectory necessary for the slave device to converge towards the resulting pose and/or orientation of the master device takes into account any obstructions and/or critical areas close to the slave device.

16. The method according to claim 1, wherein the alignment step includes a plurality of control cycles, and wherein said step of selecting the local reference frame is carried out at each of said control cycles of the alignment step, or said step of selecting the local reference frame is carried out only at a beginning of the alignment step, and/or wherein the alignment step comprises a sub-step of alignment without motion, in which the surgical instrument of the slave device is not enabled to move, and a sub-step of alignment with motion, in which the surgical instrument of the slave device is enabled to move, and wherein said step of selecting the local reference frame is carried out only during the sub-step of alignment without motion.

17. The method according to claim 1, wherein the method is used for initiating and/or preparing and/or conducting a teleoperation carried out by the robotic system for medical or surgical teleoperation.

18. The method according to claim 1, wherein, during the teleoperation step, in presence of a rotation movement about the longitudinal axis, due to manipulation by the operator, which occurs below a predetermined time threshold, the method includes:

switching the operating reference frame, from one of said local operating reference frames to the other, and/or decoupling the enslaved movements of the slave device with reference only to the movements enslaved to movements controlled by the longitudinal axis of the master device, until rolling speed of the master falls below said time threshold, and/or wherein, during a phase of limited teleoperation and/or a phase of suspended teleoperation, in which the slave device is enslaved to the master device only for some of the controllable degrees of freedom, the method includes re-evaluating which of the plurality of local operating reference frames has to be utilized for calculation of the target orientation of the master device, in the presence of a rotation movement about the longitudinal axis, due to the manipulation by the operator, which occurs below a predetermined time threshold, wherein said rotation movement about the longitudinal axis, due to the manipulation by the operator corresponds to a 180° rotation.

19. The method according to claim 1, wherein, after conclusion of the alignment step, the teleoperation step is conducted by expressing a current orientation of the target device, and the enslaved orientation of the slave device, based on the operating reference frame selected during the alignment step, or wherein the last transformation function selected during the alignment step is utilized during an entire duration of a subsequent teleoperation.

20. A robotic system for medical or surgical teleoperation, comprising at least one master device, which is hand-held, mechanically unconstrained and adapted to be moved by an operator, and at least one slave device comprising a surgical instrument adapted to be controlled by the master device, wherein the master device is functionally symmetrical with respect to a predeterminable single, longitudinal axis of the master device, wherein the system is configured to carry out the following actions:

detecting a local reference frame of the master device and the longitudinal axis thereof of the master device, with respect to a main reference frame of a workspace of the master device;

defining a plurality of local reference frames which are functionally equivalent to the local reference frame detected, said local reference frames being rotated by a respective angle about said longitudinal axis of the master device;

mapping a corresponding target reference frame in a workspace of the slave device for each of said local reference frames of the master device of said plurality of local reference frames functionally equivalent to the local reference frame detected;

selecting an operating reference frame, from said plurality of local reference frames functionally equivalent to the local reference frame detected, according to criteria for optimization of the trajectory of the slave device, wherein the system also comprises:

a control unit configured to carry out said actions of detecting, defining, mapping and selecting.

* * * * *